United States Patent
Nirogi et al.

(10) Patent No.: US 12,275,746 B2
(45) Date of Patent: Apr. 15, 2025

(54) PYRROLO[1,2-B]-2-PYRIDAZINONE COMPOUNDS AS 5-HT4 RECEPTOR AGONISTS

(71) Applicant: SUVEN LIFE SCIENCES LIMITED, Hyderabad-Telangana (IN)

(72) Inventors: Ramakrishna Nirogi, Hyderabad (IN); Anil Karbhari Shinde, Hyderabad (IN); Abdul Rasheed Mohammed, Hyderabad (IN); Vinod Kumar Goyal, Hyderabad (IN); Santosh Kumar Pandey, Hyderabad (IN); Vijay Sidram Benade, Hyderabad (IN); Venkatesh Goura, Hyderabad (IN); Venkateswarlu Jasti, Hyderabad (IN)

(73) Assignee: SUVEN LIFE SCIENCES LIMITED, Hyderabad-Telangana (IN)

( * ) Notice: Subject to any disclaimer, the term of this patent is extended or adjusted under 35 U.S.C. 154(b) by 0 days.

(21) Appl. No.: 18/724,932

(22) PCT Filed: Jan. 10, 2023

(86) PCT No.: PCT/IB2023/050192
§ 371 (c)(1),
(2) Date: Jun. 27, 2024

(87) PCT Pub. No.: WO2023/135508
PCT Pub. Date: Jul. 20, 2023

(65) Prior Publication Data
US 2025/0019386 A1    Jan. 16, 2025

(30) Foreign Application Priority Data
Jan. 11, 2022 (IN) .............. 202241001436

(51) Int. Cl.
*C07D 519/00* (2006.01)
*A61K 31/5025* (2006.01)
*A61P 1/00* (2006.01)

(52) U.S. Cl.
CPC ........ *C07D 519/00* (2013.01); *A61K 31/5025* (2013.01); *A61P 1/00* (2018.01)

(58) Field of Classification Search
CPC .................. C07D 519/00; A61K 31/5025
USPC ....................................................... 514/248
See application file for complete search history.

(56) References Cited

U.S. PATENT DOCUMENTS
2005/0228014 A1  10/2005  Marquess

FOREIGN PATENT DOCUMENTS

| WO | 2005121151 | 12/2005 |
|---|---|---|
| WO | 20060041985 | 4/2006 |
| WO | 20060052640 | 5/2006 |
| WO | 20060052889 | 5/2006 |
| WO | 20060094063 | 9/2006 |

OTHER PUBLICATIONS

European Patent Office, "International Search Report" issued Mar. 17, 2023 in PCT/IB2023/050192.
European Patent Office, "Written Opinion" issued Mar. 17, 2023 in PCT/IB2023/050192.
Drossman (ed.), "The Functional Gastrointestinal Disorders and the Rome III Process" Gastroenterology (Apr. 2006) 130(5):1377-90.
Oustamanolakis and Tack, "Prucalopride for chronic intestinal pseudo-obstruction" Aliment Pharmacol Ther. (Feb. 2012) 35(3):398-9.
Mendzelevski et al, "Assessment of the cardiac safety of prucalopride in healthy volunteers: a randomized, double-blind, placebo- and positive-controlled thorough QT study" Br J Clin Pharmacol (Feb. 2012) 73(2):203-9.
Tack et al., "Systematic review: cardiovascular safety profile of 5-HT4 agonists developed for gastrointestinal disorders" Aliment Pharmacol Ther (Apr. 2012) 35(7):745-67.
Johnson et al., "The 5-Hydroxytryptamine4 Receptor Agonists Prucalopride and PRX-03140 Increase Acetylcholine and Histamine Levels in the Rat Prefrontal Cortex and the Power of Stimulated Hippocampal [theta] Oscillations" J Pharmacol Exper Therap (Jun. 2012) 341(3):681-691.
Murray McKinnell et al., "A Multivalent Approach to the Design and Discovery of Orally Efficacious 5-HT4 Receptor Agonists" J Med Chem (2009) 52(17):5330-5343.
Suzuki et al., "Synthesis and Evaluation of Novel 2-Oxo-1,2-dihydro-3-quinolinecarboxamide Derivatives as Potent and Selective Serotonin 5-HT4 Receptor Agonists" Chem Pharm Bull (2001) 49(1):29-39.
Long et al., "Discovery, oral pharmacokinetics and in vivo efficacy of velusetrag, a highly selective 5-HT4 receptor agonist that has achieved proof-of-concept in patients with chronic idiopathic constipation" Bioorg & Med Chem Letters (2012) 22:6048-6052.
The International Bureau of WIPO, "International Preliminary Report on Patentability" issued Jun. 20, 2024 and "Notification Concerning Transmittal of International Preliminary Report on Patentability" mailed Jul. 25, 2024 in PCT Application No. PCT/IB2023/050192.

*Primary Examiner* — Kahsay Habte
(74) *Attorney, Agent, or Firm* — IPHORGAN LTD.

(57) ABSTRACT

The present invention relates to pyrrolo[1,2-b]-2-pyridazinone compounds of formula (I), or their isotopic forms, stereoisomers, or pharmaceutically acceptable salts thereof as 5-HT$_4$ receptor agonists. The present invention also describes methods of making such compounds, pharmaceutical compositions comprising such compounds, and their use in the treatment of gastrointestinal disease or disorder.

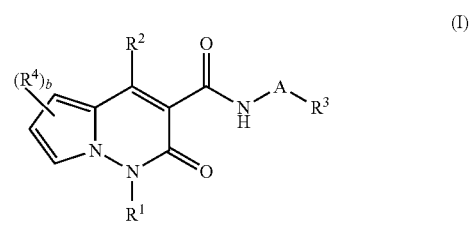

7 Claims, 2 Drawing Sheets

Data represent as Mean + SEM of % colonic transit. **$p<0.01$ Vs Vehicle, one way ANOVA followed by Dunnett's multiple comparisons test (n=8-10/group)

Data represent as Mean + SEM of % change in number of spikes. $*p<0.05$, $p<0.01$, $*p<0.001$ Vs Vehicle, two way ANOVA followed by Bonferroni multiple comparisons test (n=5-8/group)

PYRROLO[1,2-B]-2-PYRIDAZINONE COMPOUNDS AS 5-HT4 RECEPTOR AGONISTS

CROSS REFERENCE TO RELATED APPLICATIONS

This application is a national stage completion application of PCT Application No. PCT/IB2023/050192, filed Jan. 10, 2023, and claims priority from India Application No. 202241001436, filed Jan. 11, 2022. Each of these applications is incorporated by reference herein in its entirety.

FIELD OF INVENTION

The present invention relates to pyrrolo[1,2-b]-2-pyridazinone compounds of formula (I), or their isotopic forms, stereoisomers, or pharmaceutically acceptable salts thereof as 5-HT$_4$ receptor agonists. The present invention also describes methods of making such compounds, pharmaceutical compositions comprising such compounds, and their use in the treatment of gastrointestinal disease or disorder.

BACKGROUND OF THE INVENTION

Extensive literature precedence suggests the potential of serotonin type 4 (5-HT$_4$) receptor agonists for the treatment of reduced and/or abnormal motility of the gastrointestinal tract. This reduced and/or abnormal motility may be due to various disorders like irritable bowel syndrome (IBS) (IBS with predominant constipation, IBS with predominant diarrhea, IBS with mixed bowel habits, and IBS unclassified), chronic constipation, functional dyspepsia, gastroparesis, gastroesophageal reflux disorder, post-operative ileus, intestinal pseudo-obstruction, drug-induced delayed transit, Crohn's disease, celiac disease, etc. These disorders have a profound effect on patients' quality of life and impose a substantial economic burden (*Gastroenterology*. 2006 April; 130(5):1377-90).

The 5-HT$_4$ receptor agonist activates the release of acetylcholine from intrinsic cholinergic neurons to stimulate smooth muscle contractions in the gastrointestinal tract. The 5-HT$_4$ receptor agonists such as cisapride and tegaserod were successfully developed for treating gastrointestinal hypomotility in the upper or lower gastrointestinal tract. Prucalopride, another 5-HT$_4$ receptor agonist approved for the treatment of chronic intestinal pseudo-obstruction (*Aliment Pharmacol Ther.* 2012 February; 35(3):398-9). Drugs interacting with the hERG potassium channel are associated with QT interval prolongation, which may lead to life-threatening arrhythmias (*Br J Clin Pharmacol*. 2012 February; 73(2):203-9). Both prokinetic agents, cisapride and tegaserod, showed poor selectivity for 5-HT$_4$ receptors and showed potent interaction with hERG potassium channels and, as a consequence, showed poor benefit to risk profile. Both prokinetic agents have been withdrawn from the global market due to cardiovascular risk (*Aliment Pharmacol Ther.* 2012 April, 35(7):745-67). Prucalopride has extensive brain penetration (*Journal of Pharmacology and Experimental Therapeutics* June 2012, 341(3)681-691) which may not be an ideal requirement for the compounds intended to work on peripheral receptors. Accordingly, there exists an urgent need for new 5-HT$_4$ receptor agonists having desired pharmacological effect with no/minimal brain penetration and side effect profile. It is also expected that such agents should have minimal or no side effects.

WO2006052640, WO2006052889, WO2006094063 and US2005228014A1 disclose 5-HT$_4$ receptor agonist. Murray et al. describe 5-HT$_4$ receptor agonists for the potential treatment of gastrointestinal motility-related disorders (*Journal of Medicinal Chemistry* (2009), 52(17), 5330-5343). Suzuki et al. describe novel 2-oxo-1,2-dihydro-3-quinoline carboxamide derivatives as potent and selective serotonin 5-HT$_4$ receptor agonists useful in improving gastrointestinal dysfunction (*Chem. Pharm. Bull.* 49(1) 29-39 (2001). Long et al. describe velusetrag, a highly selective 5-HT$_4$ receptor agonist for chronic idiopathic constipation (*Bioorganic & Medicinal Chemistry Letters* 22 (2012) 6048-6052).

The present invention provides potent and selective 5-HT$_4$ receptor agonists with acceptable pharmacokinetic properties including good oral bioavailability, no/minimal brain penetration, no interaction with hERG potassium channel thereby no cardiovascular liability, and showed robust efficacy in animal models.

SUMMARY OF THE INVENTION

In one aspect, the present invention relates to a compound of formula (I),

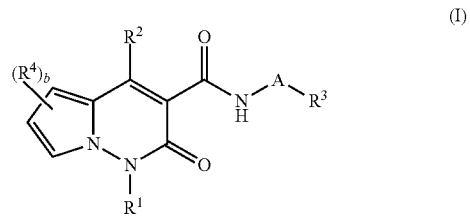

or an isotopic form, a stereoisomer or a pharmaceutically acceptable salt thereof,
wherein:
R$^1$ represents hydrogen, alkyl or cycloalkyl;
R$^2$ represents hydrogen, hydroxy, halogen, alkyl or cycloalkyl;
A is a heterocyclic ring selected from the group consisting of:

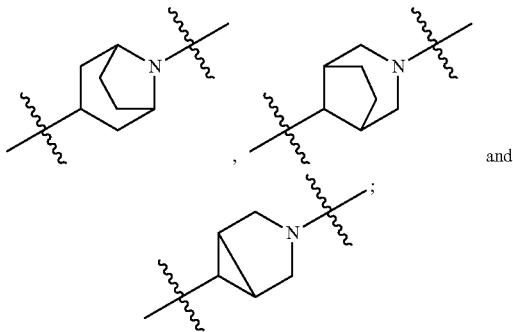

R$^3$ is hydrogen or selected from the group consisting of:

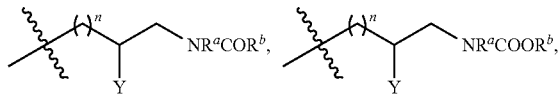

-continued

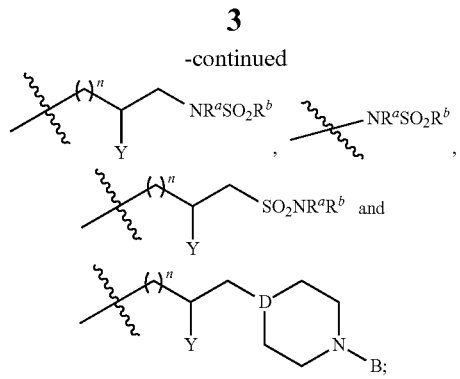

B is selected from hydrogen, alkyl, cycloalkyl, haloalkyl, hydroxyalkyl, —SO₂-alkyl, —COCH₃, —COO-alkyl, or —CO—(CH₂)$_m$—OH; wherein, m is an integer from 0 to 5;

Y at each occurrence is independently selected from hydrogen, hydroxy, halogen, haloalkyl, hydroxyalkyl, —COOH, —COO-alkyl, —O-alkyl, —S-alkyl or —NR$^a$R$^b$;

D represents CH or N;

n is an integer from 0 to 5;

R$^a$ at each occurrence is independently selected from hydrogen, alkyl, cycloalkyl or alkoxy;

R$^b$ at each occurrence is independently selected from hydrogen, alkyl, cycloalkyl or alkoxy;

R$^4$ represents hydrogen, hydroxy, halogen, alkyl or cycloalkyl; and b represents 1 to 3.

In another aspect, the present invention relates to the processes for preparing the compound of formula (I), or an isotopic form, a stereoisomer or a pharmaceutically acceptable salt thereof.

In yet another aspect, the present invention relates to a pharmaceutical composition comprising a therapeutically effective amount of at least one compound of formula (I), or an isotopic form, a stereoisomer or a pharmaceutically acceptable salt thereof and pharmaceutically acceptable excipients or carriers.

In yet another aspect, the present invention relates to the compound of formula (I), or an isotopic form, a stereoisomer or a pharmaceutically acceptable salt thereof, for use as a 5-Hydroxytryptamine 4 receptor agonist.

In yet another aspect, the present invention relates to the compound of formula (I), or an isotopic form, a stereoisomer or a pharmaceutically acceptable salt thereof, for use in the treatment of gastrointestinal disease or disorder.

In another aspect, the present invention relates to a method for the treatment of gastrointestinal disease or disorder, comprising administering to a patient in need thereof, a therapeutically effective amount of the compound of formula (I), or an isotopic form, a stereoisomer or a pharmaceutically acceptable salt thereof.

In yet another aspect, the present invention relates to use of the compound of formula (I), or an isotopic form, a stereoisomer or a pharmaceutically acceptable salt thereof, for the manufacture of a medicament for the treatment of gastrointestinal disease or disorder.

In yet another aspect, the present invention relates to a pharmaceutical composition comprising a therapeutically effective amount of at least one of the compounds of formula (I), or an isotopic form, a stereoisomer or a pharmaceutically acceptable salt thereof and pharmaceutically acceptable excipients or carriers, for use in the treatment of gastrointestinal disease or disorder.

DETAILED DESCRIPTION OF THE INVENTION

Figure 1:
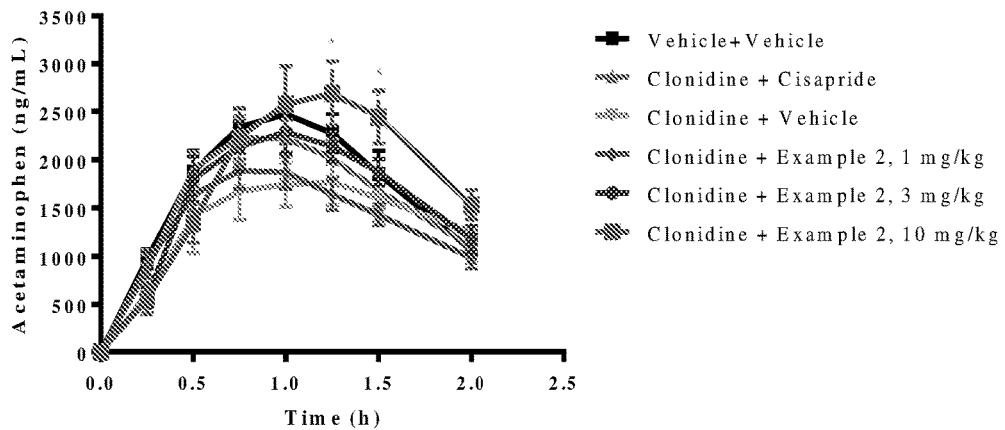
FIG. 1 depicts the gastric emptying effect of Example 2 in Beagle dogs.

Unless otherwise stated, the following terms used in the specification and claims have the meanings given below:

The term, "alkyl" as used herein refers to a linear or branched chain aliphatic hydrocarbon. Examples of alkyl include methyl, ethyl, n-propyl, isopropyl, n-butyl, isobutyl, sec-butyl, tert-butyl and the like.

The term, "cycloalkyl" as used herein refers to a saturated monocyclic hydrocarbon ring containing from three to six carbon atoms. Examples of cycloalkyl group include cyclopropyl, cyclobutyl, cyclopentyl and cyclohexyl.

The term, "alkoxy" as used herein refers to an alkyl group singularly bonded to an oxygen atom. Examples of the alkoxy group include methoxy, ethoxy, propoxy, methoxypropoxy, butoxy and the like.

The term, "halogen" or "halo" as used herein refers to fluorine, chlorine, bromine or iodine. Preferably, halogen is fluorine, chlorine or bromine. More preferably halogen is fluorine or chlorine.

The term, "haloalkyl" as used herein refers to alkyl as defined above wherein one or more hydrogen of the same or different carbon atom is substituted with same or different halogens. Examples of the haloalkyl include fluoromethyl, chloromethyl, fluoroethyl, difluoromethyl, dichloromethyl, trifluoromethyl, difluoroethyl and the like.

The term, "hydroxyalkyl" as used herein refers to alkyl as defined above wherein one or more hydrogen of the same or different carbon atom is substituted with hydroxy group. Examples of the hydroxyalkyl include hydroxymethyl, hydroxyethyl, hydroxypropyl, and hydroxybutyl.

The term "protecting group" or "PG" as used herein refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, tert-Butoxycarbonyl (Boc), benzyloxycarbonyl (Cbz) and 9-fluorenylmethyloxycarbonyl (Fmoc).

The phrase, "therapeutically effective amount" is defined as an amount of a compound of the present invention that (i) treats the particular disease, condition or disorder (ii) eliminates one or more symptoms of the particular disease, condition or disorder (iii) delays the onset of one or more symptoms of the particular disease, condition or disorder described herein.

The term, "isotopic form" as used herein refers to the compound of formula (I) wherein one or more atoms of compound of formula (I) are substituted by their respective isotopes. For example, isotopes of hydrogen include ²H (deuterium) and ³H (tritium).

The term, "stereoisomer" as used herein refers to isomers of the compound of formula (I) that differ in the arrangement of their atoms in space. Compounds disclosed herein may exist as a single stereoisomer, racemates and/or mixtures of enantiomers and/or diastereomers. All such single stereoisomer, racemates and mixtures thereof are intended to be within the scope of the present invention.

The term, "pharmaceutically acceptable salt" as used herein refers to salts of the active compound i.e. the compound of formula (I), and are prepared by reaction with the appropriate acid or acid derivative, depending on the particular substituents found on the compounds described herein.

The term, "gastrointestinal disease or disorder" as used herein refers to diseases or disorders related gastrointestinal tract that includes but not limited to irritable bowel syndrome (IBS), IBS with predominant constipation, IBS with predominant diarrhea, IBS with mixed bowel habits, IBS unclassified, chronic constipation, functional dyspepsia, gastroparesis, gastroesophageal reflux disorder, post-operative ileus, intestinal pseudo-obstruction, drug-induced delayed transit, Barrett esophagus, intestinal pseudoileus, acute gastritis, chronic gastritis, gastric ulcer, duodenal ulcer, non-ulcer dyspepsia, Crohn's disease, celiac disease and/or delayed gastric emptying caused by gastric neurosis.

EMBODIMENTS

The present invention encompasses all the compounds described by the compound of formula (I) without any limitation, however, preferred aspects and elements of the invention are discussed herein in the form of the following embodiments.

In one embodiment, the present invention relates to the compound of formula (I), or an isotopic form, a stereoisomer, or a pharmaceutically acceptable salt thereof, wherein, A is

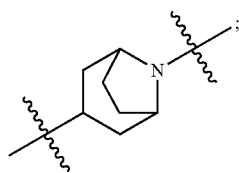 [SMILES: *C1CC2CCC(C1)N2*]

$R^3$ is hydrogen or selected from the group consisting of:

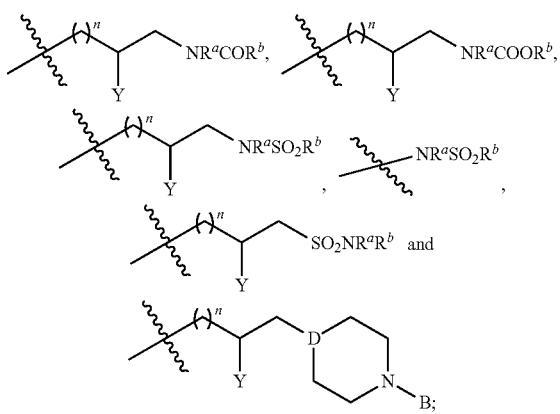

wherein B, D, Y, $R^a$, $R^b$ and n are as defined in the first aspect.

In another embodiment, the present invention relates to the compound of formula (I), or an isotopic form, a stereoisomer, or a pharmaceutically acceptable salt thereof, wherein, A is

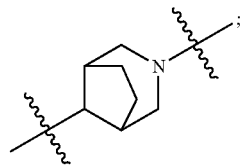 [SMILES: *C1C2CCC1CN(*)C2]

$R^3$ is hydrogen or selected from the group consisting of:

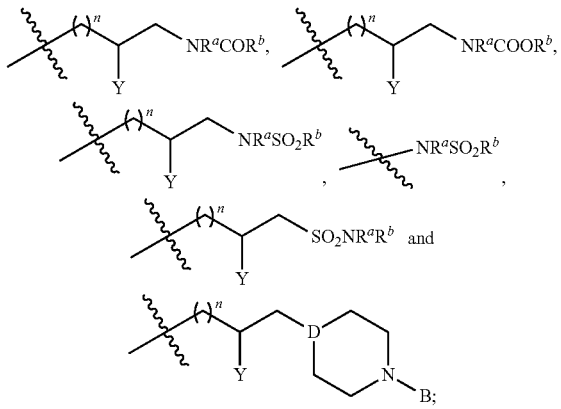

wherein B, D, Y, $R^a$, $R^b$ and n are as defined in the first aspect.

In another embodiment, the present invention relates to the compound of formula (I), or an isotopic form, a stereoisomer, or a pharmaceutically acceptable salt thereof, wherein, A is

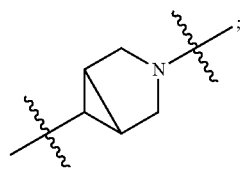 [SMILES: *C1C2CN(*)CC12]

$R^3$ is hydrogen or selected from the group consisting of:

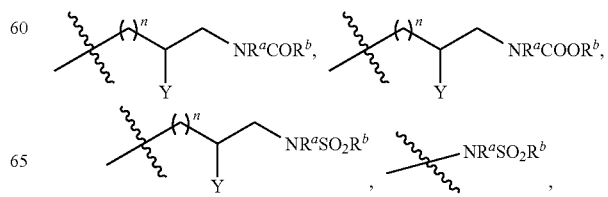

-continued

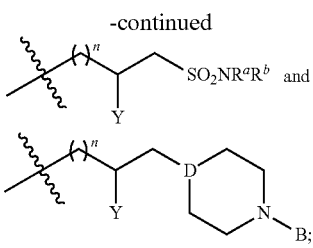

wherein B, D, Y, $R^a$, $R^b$ and n are as defined in the first aspect.

In another embodiment of the present invention relates to the compound of formula (I), or an isotopic form, a stereoisomer, or a pharmaceutically acceptable salt thereof, wherein, A is

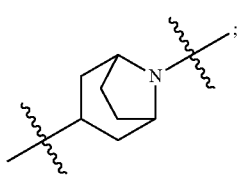 [SMILES: *C1CC2CCC(C1)N2*]

$R^2$ is hydrogen or hydroxy;
$R^3$ is selected from the group consisting of:

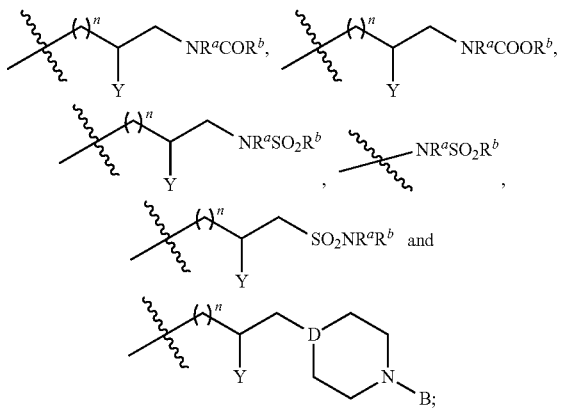

B is selected from $-SO_2$-alkyl, $-COCH_3$, $-COO$-alkyl, alkyl, cycloalkyl, haloalkyl, hydroxyalkyl or $-CO-(CH_2)_m-OH$; wherein m is an integer from 0 to 5;

Y at each occurrence is independently selected from hydrogen or hydroxy;

D represents CH or N;

n is an integer from 0 to 5;

$R^a$ at each occurrence is independently selected from hydrogen or alkyl;

$R^b$ at each occurrence is independently selected from hydrogen, alkyl, cycloalkyl or alkoxy; and $R^4$ represents hydrogen.

In yet another embodiment of the present invention relates to the compound of formula (I), or an isotopic form, a stereoisomer, or a pharmaceutically acceptable salt thereof, wherein, $R^3$ is

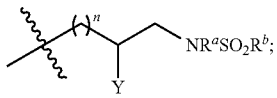

wherein, Y is hydrogen or hydroxy; $R^a$ is hydrogen or alkyl;
$R^b$ is alkyl; and n is 0, 1 or 2.

In yet another embodiment of the present invention relates to the compound of formula (I), or an isotopic form, a stereoisomer, or a pharmaceutically acceptable salt thereof, wherein, $R^3$ is

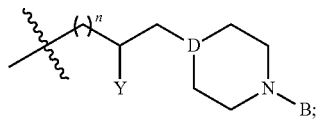

wherein, Y is hydrogen or hydroxy; B is $-SO_2$-alkyl, D is N; and n is 0, 1 or 2.

In yet another embodiment of the present invention relates to the compound of formula (I), or an isotopic form, a stereoisomer, or a pharmaceutically acceptable salt thereof, wherein, $R^3$ is

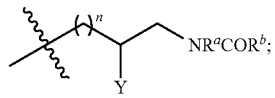

wherein, Y is hydrogen or hydroxy; $R^a$ is hydrogen or alkyl;
$R^b$ is alkyl; and n is 0, 1 or 2.

In yet another embodiment of the present invention relates to the compound of formula (I), or an isotopic form, a stereoisomer or a pharmaceutically acceptable salt thereof, wherein, $R^3$ is

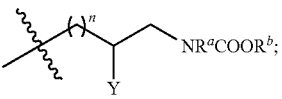

wherein, Y is hydrogen or hydroxy; $R^a$ is hydrogen or alkyl; $R^b$ is alkyl; and n is 0, 1 or 2.

In yet another embodiment of the present invention relates to the compound of formula (I), or an isotopic form, a stereoisomer, or a pharmaceutically acceptable salt thereof, wherein, $R^1$ is hydrogen or alkyl. In some embodiments, B is $-SO_2$-alkyl, or $-COCH_3$.

In another embodiment of the present invention relates to the compound of formula (I), or an isotopic form, a stereoisomer or a pharmaceutically acceptable salt thereof is selected from the group consisting of:

(R)—N-{8-[2-Hydroxy-3-[(N-methyl) methanesulfonamido]propyl]-8-azabicyclo[3.2.1]oct-3-yl}[1-isopropyl-2-oxo-1,2-dihydro pyrrolo[1,2-b]pyridazine]-3-carboxamide;

(R)—N-{8-[2-Hydroxy-3-[(N-methyl) methanesulfonamido]propyl]-8-azabicyclo[3.2.1]oct-3-yl}[1-isopropyl-2-oxo-1,2-dihydro pyrrolo[1,2-b]pyridazine]-3-carboxamide L-(+)-tartrate;

(S)—N-{8-[2-Hydroxy-3-[(N-methyl) methanesulfonamido]propyl]-8-azabicyclo[3.2.1]oct-3-yl}[1-isopropyl-2-oxo-1,2-dihydro pyrrolo[1,2-b]pyridazine]-3-carboxamide;

(S)—N-{8-[2-Hydroxy-3-[(N-methyl) methanesulfonamido]propyl]-8-azabicyclo[3.2.1]oct-3-yl}[1-isopropyl-2-oxo-1,2-dihydro pyrrolo[1,2-b]pyridazine]-3-carboxamide L(+)-tartarate;

Racemic-N-{8-[2-Hydroxy-3-[(N-methyl) methanesulfonamido]propyl]-8-azabicyclo[3.2.1]oct-3-yl}[1-isopropyl-2-oxo-1,2-dihydro pyrrolo[1,2-b]pyridazine]-3-carboxamide;

Racemic-N-{8-[2-Hydroxy-3-[(N-methyl) methanesulfonamido]propyl]-8-azabicyclo[3.2.1]oct-3-yl}[1-isopropyl-2-oxo-1,2-dihydro pyrrolo[1,2-b]pyridazine]-3-carboxamide L(+)-tartarate;

(R)—N-{8-[2-Hydroxy-3-[(N-methyl) methanesulfonamido]propyl]-8-azabicyclo[3.2.1]oct-3-yl}[4-hydroxy-1-isopropyl-2-oxo-1,2-dihydro pyrrolo[1,2-b]pyridazine]-3-carboxamide;

(R)—N-{8-[2-Hydroxy-3-[(N-methyl) methanesulfonamido]propyl]-8-azabicyclo[3.2.1]oct-3-yl}[4-hydroxy-1-isopropyl-2-oxo-1,2-dihydro pyrrolo[1,2-b]pyridazine]-3-carboxamide L-(+)-tartrate;

(S)—N-{8-[2-Hydroxy-3-[(N-methyl) methanesulfonamido]propyl]-8-azabicyclo[3.2.1]oct-3-yl}[4-hydroxy-1-isopropyl-2-oxo-1,2-dihydro pyrrolo[1,2-b]pyridazine]-3-carboxamide;

(S)—N-{8-[2-Hydroxy-3-[(N-methyl) methanesulfonamido]propyl]-8-azabicyclo[3.2.1]oct-3-yl}[4-hydroxy-1-isopropyl-2-oxo-1,2-dihydro pyrrolo[1,2-b]pyridazine]-3-carboxamide L-(+)-tartrate;

Racemic-N-{8-[2-Hydroxy-3-[(N-methyl) methanesulfonamido]propyl]-8-azabicyclo[3.2.1]oct-3-yl}[4-hydroxy-1-isopropyl-2-oxo-1,2-dihydro pyrrolo[1,2-b]pyridazine]-3-carboxamide;

Racemic-N-{8-[2-Hydroxy-3-[(N-methyl) methanesulfonamido]propyl]-8-azabicyclo[3.2.1]oct-3-yl}[4-hydroxy-1-isopropyl-2-oxo-1,2-dihydro pyrrolo[1,2-b]pyridazine]-3-carboxamide L-(+)-tartrate;

(R)—N-{8-[2-Hydroxy-3-(methanesulfonamido) propyl]-8-azabicyclo[3.2.1]oct-3-yl}[1-isopropyl-2-oxo-1,2-dihydro pyrrolo[1,2-b]pyridazine]-3-carboxamide;

(R)—N-{8-[2-Hydroxy-3-(methanesulfonamido) propyl]-8-azabicyclo[3.2.1]oct-3-yl}[1-isopropyl-2-oxo-1,2-dihydro pyrrolo[1,2-b]pyridazine]-3-carboxamide L-(+)-tartarate;

(R)—N-{8-[2-Hydroxy-3-[(N-methyl) acetamido]propyl]-8-azabicyclo[3.2.1]oct-3-yl}[1-isopropyl-2-oxo-1,2-dihydro pyrrolo[1,2-b]pyridazine]-3-carboxamide;

(R)—N-{8-[2-Hydroxy-3-[(N-methyl) acetamido]propyl]-8-azabicyclo[3.2.1]oct-3-yl}[1-isopropyl-2-oxo-1,2-dihydro pyrrolo[1,2-b]pyridazine]-3-carboxamide L-(+)-tartrate;

(R)—N-{8-[2-Hydroxy-3-[(1-methanesulfonyl piperazin)-4-yl]propyl]-8-azabicyclo[3.2.1]oct-3-yl}[1-isopropyl-2-oxo-1,2-dihydro pyrrolo[1,2-b]pyridazin]-3-carboxamide;

(R)—N-{8-[2-Hydroxy-3-[(1-methanesulfonyl piperazin)-4-yl]propyl]-8-azabicyclo[3.2.1]oct-3-yl}[1-isopropyl-2-oxo-1,2-dihydro pyrrolo[1,2-b]pyridazin]-3-carboxamide L(+)tartarate;

(R)—N-{8-[2-Hydroxy-3-[(1-methanesulfonyl piperazin)-4-yl]propyl]-8-azabicyclo[3.2.1]oct-3-yl}[4-hydroxy-1-isopropyl-2-oxo-1,2-dihydro pyrrolo[1,2-b]pyridazin]-3-carboxamide;

(R)—N-{8-[2-Hydroxy-3-[(1-methanesulfonyl piperazin)-4-yl]propyl]-8-azabicyclo[3.2.1]oct-3-yl}[4-hydroxy-1-isopropyl-2-oxo-1,2-dihydro pyrrolo[1,2-b]pyridazin]-3-carboxamide L-(+)-tartrate;

N-{8-[3-[(N-Methyl) methanesulfonamido]propyl]-8-azabicyclo[3.2.1]oct-3-yl}[1-isopropyl-2-oxo-1,2-dihydro pyrrolo[1,2-b]pyridazine]-3-carboxamide;

N-{8-[3-[(N-Methyl) methanesulfonamido]propyl]-8-azabicyclo[3.2.1]oct-3-yl}[1-isopropyl-2-oxo-1,2-dihydro pyrrolo[1,2-b]pyridazine]-3-carboxamide L-(+)-tartrate;

N-{8-[3-[methanesulfonamido]propyl]-8-azabicyclo[3.2.1]oct-3-yl}[1-isopropyl-2-oxo-1,2-dihydro pyrrolo[1,2-b]pyridazine]-3-carboxamide;

N-{8-[3-[methanesulfonamido]propyl]-8-azabicyclo[3.2.1]oct-3-yl}[1-isopropyl-2-oxo-1,2-dihydro pyrrolo[1,2-b]pyridazine]-3-carboxamide L-(+)-tartrate;

N-{8-[3-Isopropylsulfonylaminopropyl]-8-azabicyclo[3.2.1]oct-3-yl}[1-isopropyl-2-oxo-1,2-dihydro pyrrolo[1,2-b]pyridazin]-3-carboxamide;

N-{8-[3-Isopropylsulfonylaminopropyl]-8-azabicyclo[3.2.1]oct-3-yl}[1-isopropyl-2-oxo-1,2-dihydro pyrrolo[1,2-b]pyridazin]-3-carboxamide L-(+)-tartrate;

N-{8-[2-Methanesulfonylaminoethyl]-8-azabicyclo[3.2.1]oct-3-yl}[1-isopropyl-2-oxo-1,2-dihydro pyrrolo[1,2-b]pyridazin]-3-carboxamide;

N-{8-[2-Methanesulfonylaminoethyl]-8-azabicyclo[3.2.1]oct-3-yl}[1-isopropyl-2-oxo-1,2-dihydro pyrrolo[1,2-b]pyridazin]-3-carboxamide L-(+)-tartrate;

N-{8-[2-Isopropylsulfonylaminoethyl]-8-azabicyclo[3.2.1]oct-3-yl}[1-isopropyl-2-oxo-1,2-dihydro pyrrolo[1,2-b]pyridazin]-3-carboxamide;

N-{8-[2-Isopropylsulfonylaminoethyl]-8-azabicyclo[3.2.1]oct-3-yl}[1-isopropyl-2-oxo-1,2-dihydro pyrrolo[1,2-b]pyridazin]-3-carboxamide L-(+)-tartrate;

N-{8-[3-Acetamidopropyl]-8-azabicyclo[3.2.1]oct-3-yl}[1-isopropyl-2-oxo-1,2-dihydro pyrrolo[1,2-b]pyridazin]-3-carboxamide;

N-{8-[3-Acetamidopropyl]-8-azabicyclo[3.2.1]oct-3-yl}[1-isopropyl-2-oxo-1,2-dihydro pyrrolo[1,2-b]pyridazin]-3-carboxamide L-(+)-tartrate;

N-{8-[3-Carbomethoxyaminopropyl]-8-azabicyclo[3.2.1]oct-3-yl}[1-isopropyl-2-oxo-1,2-dihydro pyrrolo[1,2-b]pyridazin]-3-carboxamide;

N-{8-[3-Carbomethoxyaminopropyl]-8-azabicyclo[3.2.1]oct-3-yl}[1-isopropyl-2-oxo-1,2-dihydro pyrrolo[1,2-b]pyridazin]-3-carboxamide L-(+)-tartrate;

N-{8-[2-Carbomethoxyaminoethyl]-8-azabicyclo[3.2.1]oct-3-yl}[1-isopropyl-2-oxo-1,2-dihydro pyrrolo[1,2-b]pyridazin]-3-carboxamide;

N-{8-[2-Carbomethoxyaminoethyl]-8-azabicyclo[3.2.1]oct-3-yl}[1-isopropyl-2-oxo-1,2-dihydro pyrrolo[1,2-b]pyridazin]-3-carboxamide L-(+)-tartrate;

N-{8-[2-(4-Acetyl piperazin-1-yl) ethyl]-8-azabicyclo[3.2.1]oct-3-yl}[1-isopropyl-2-oxo-1,2-dihydro pyrrolo[1,2-b]pyridazine]-3-carboxamide;

N-{8-[2-(4-Acetyl piperazin-1-yl) ethyl]-8-azabicyclo[3.2.1]oct-3-yl}[1-isopropyl-2-oxo-1,2-dihydro pyrrolo[1,2-b]pyridazine]-3-carboxamide L-(+)-tartrate;

N-{8-[2-(4-Acetyl piperazin-1-yl) ethyl]-8-azabicyclo[3.2.1]oct-3-yl}[4-hydroxy-1-isopropyl-2-oxo-1,2-dihydropyrrolo[1,2-b]pyridazine]-3-carboxamide; and N-{8-[2-(4-Acetyl piperazin-1-yl) ethyl]-8-azabicyclo [3.2.1]oct-3-yl}[4-hydroxy-1-isopropyl-2-oxo-1,2-dihydropyrrolo[1,2-b]pyridazine]-3-carboxamide L-(+)-tartrate.

In another embodiment, the present invention relates to the processes for the preparation of the compound of formula (I) as described below.

Experimental Procedures:

Scheme-1 depicts general processes for preparation of the compound of formula (I), wherein: T is hydrogen or alkyl; PG is protecting group; $R^1$, $R^2$, $R^3$, $R^4$, A and 'b' are as defined above.

Step-2: Preparation of Compound of Formula 3

The compound of formula 3 is obtained by reacting the compound of formula 2 either with trifluoroacetic acid, ethanolic HCl, methanolic HCl or IPA HCl in presence of a solvent selected from DCM, 1,2-dichloroethane, chlorobenzene, THF and like at temperature 0 to 10° C. followed by stirring at room temperature for 18 to 24 h.

Step-3: Preparation of Compound of Formula (I)

Method-A: The compound of formula (I) is obtained by adding an organic base such as $K_2CO_3$, $Cs_2CO_3$ or $Na_2CO_3$ to a stirred solution of the compound of formula 1 (wherein T is alkyl) and an amine of formula

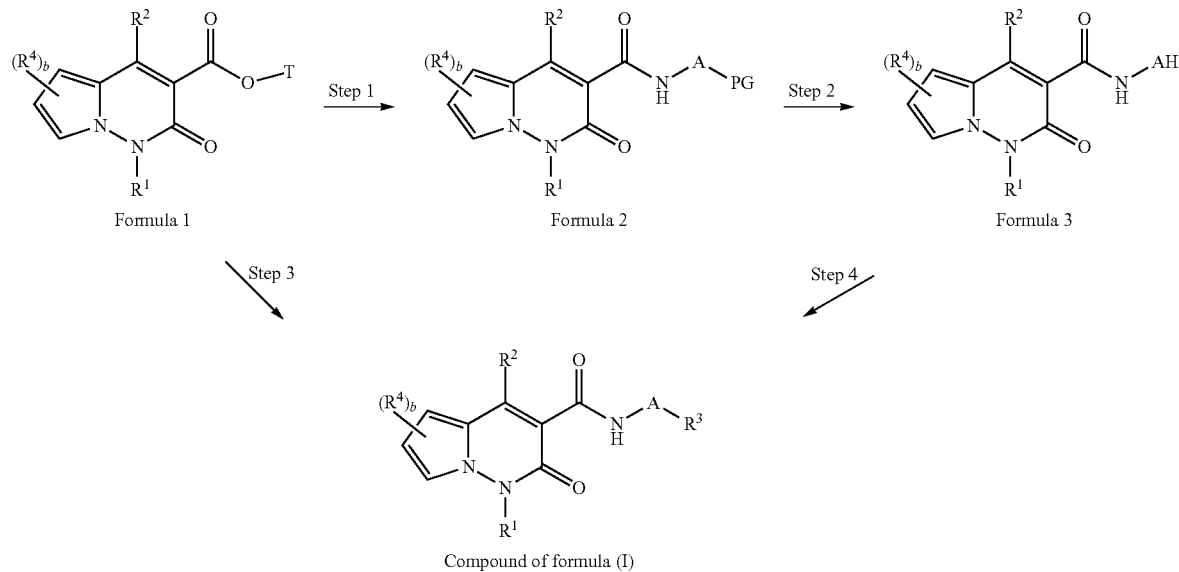

Step-1: Preparation of Compound of Formula 2

Method-A: The compound of formula 2 is obtained by reacting the compound of formula 1 (wherein T is hydrogen) with a selected amine of formula

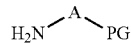

in presence of coupling reagent selected from DIPEA, TBTU, HATU, DCC, HOBt or EDC·HCl, and a solvent selected from DMF, THF, DCM, 1,4-dioxane or a mixture of two or more above said solvents at room temperature for 1 to 10 h; or Method-B: The compound of formula 2 is obtained by adding an organic base such as $K_2CO_3$, $Cs_2CO_3$ or $Na_2CO_3$ to a stirred solution of the compound of formula 1 (wherein T is alkyl) and an amine of formula

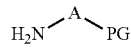

in a solvent selected from toluene, DMF, DMSO, $CH_3CN$, DCM and 1,4-dioxane at room temperature and heating at reflux temperature for 10 to 24 h preferably 20 h.

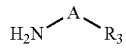

in a solvent selected from toluene, DMF, DMSO, $CH_3CN$, DCM and 1,4-dioxane at room temperature and heating at reflux temperature for 20 h; or Method-B: The compound of formula (I) is obtained by reacting the compound of formula 1 (wherein T is hydrogen) with an amine of formula

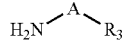

in presence of coupling reagents selected from DIPEA, HATU, DCC, or EDC·HCl and a solvent selected from DMF, THF, DCM, 1,4-dioxane or a mixture of two or more above said solvent at room temperature for 15 to 25 h.

Step-4: Preparation of Compound of Formula (I)

Method-A: The compound of formula (I) is obtained by reacting the compound of formula 3 with oxiranes of formula

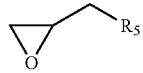

(Wherein, $R_5$ is —$NR^aCOR^b$, —$NR^aCOOR^b$, —$NR^aSO_2R^b$, —$SO_2NR^aR^b$ or

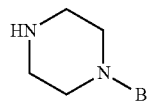

) in presence of coupling reagent selected from organic bases such as triethylamine, DIPEA, or inorganic bases such as $K_2CO_3$, or $Cs_2CO_3$ and a solvent selected from protic solvents such as methanol or ethanol, or aprotic solvents such as DMF, DMSO, $CH_3CN$, DCM and 1,4-dioxane at room temperature for 20 to 30 h; or Method-B: The compound of formula (I) is obtained by adding inorganic bases such as $K_2CO_3$, $Cs_2CO_3$ or $Na_2CO_3$ to a stirred solution of the compound of formula 3 and compound of formula (Br—$R^3$) in a solvent selected from protic solvents such as methanol or ethanol, or aprotic solvents such as DMF, DMSO, $CH_3CN$, DCM and 1,4-dioxane at room temperature and heated at reflux temperature for 8 h.

Scheme-2

Scheme-2 depicts general processes for preparation of the compound of formula (I), wherein: X is halogen; R is alkyl; $R^1$, $R^2$, $R^3$, $R^4$, A and 'b' are as defined above.

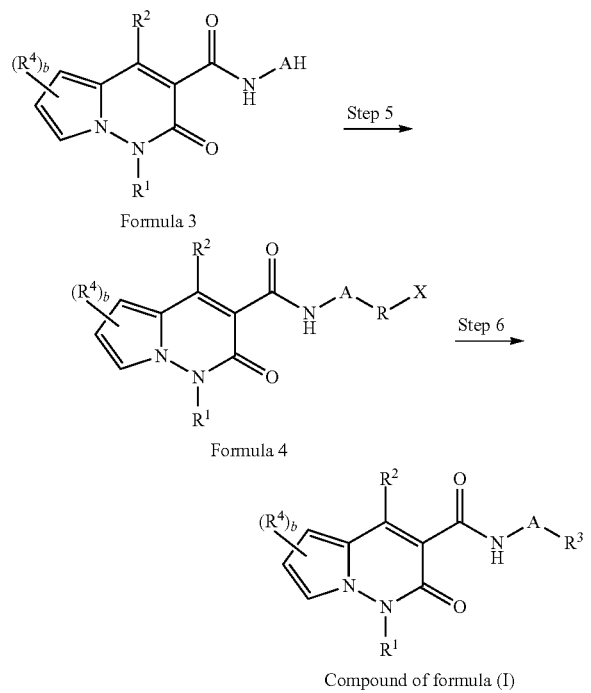

Preparation of Compound of Formula 3

The compound of formula 3 is obtained through the procedure as described in Scheme-1.

Step-5: Preparation of Compound of Formula 4

The compound of formula 4 is prepared by alkylating the compound of formula 3 with a compound of formula X—$(CH_2)_n$—X (wherein X represents either same or different halogen atom at each occurrence and n is an integer from 1 to 5) using an inorganic base such as $K_2CO_3$, $Cs_2CO_3$ or $Na_2CO_3$ in presence of solvents selected from $CH_3CN$, DCM, DMF or DMSO at reflux temperature for 20 to 25 h.

Step-6: Preparation of Compound of Formula (I)

The compound of formula (I) is prepared by reacting the compound of formula 4 with $HNR^aCOR^b$, $HNR^aCOOR^b$, $HNR^aSO_2R^b$ or

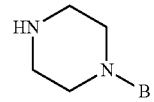

using an inorganic base such as $K_2CO_3$, $Cs_2CO_3$ or $Na_2CO_3$ in presence of solvents selected from $CH_3CN$, DCM, DMF or DMSO at reflux temperature for 20 to 25 h.

Preparation of Pharmaceutically Acceptable Salt of the Compound of Formula (I)

The compound of formula (I) can optionally be converted into its pharmaceutically acceptable salt by reaction with the appropriate acid or acid derivative. Suitable pharmaceutically acceptable salts will be apparent to those skilled in the art. The salts are formed with inorganic acids e.g., hydrochloric, hydrobromic, sulfuric, nitric and phosphoric acid, or organic acids e.g., oxalic, succinic, maleic, acetic, fumaric, citric, malic, tartaric, benzoic, toluic, toluenesulfonic, benzenesulfonic, methanesulfonic, camphorsulfonic or naphthalenesulfonic acid.

Preparation of Stereoisomers of the Compound of Formula (I)

The stereoisomers of compounds of formula (I) may be prepared by one or more conventional ways presented below:

a. One or more of the reagents may be used in their optically active form.

b. The mixture of stereoisomers may be resolved by conventional methods such as forming diastereomeric salts with chiral acids, chiral amines, chiral amino alcohols, or chiral amino acids. The resulting mixture of diastereomers may then be separated by methods such as fractional crystallization, chromatography and the like, which is followed by an additional step of isolating the optically active product from the resolved material/salt.

c. The mixture of stereoisomers may be resolved by conventional methods such as microbial resolution, resolving the diastereomeric salts formed with chiral acids or chiral bases. Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like.

In another embodiment, the suitable pharmaceutically acceptable salt includes hydrochloride, hydrobromide, oxalate, fumarate, tartrate, maleate, benzoate and succinate.

In another embodiment of the present invention, the compound of formula (I) or a stereoisomer, or a pharmaceutically acceptable salt thereof are 5-Hydroxytryptamine 4 receptor agonists.

In another embodiment, the present invention relates to a method for the treatment of gastrointestinal disease or disorder related to 5-Hydroxytryptamine 4 receptor selected from irritable bowel syndrome, chronic constipation, functional dyspepsia, gastroparesis, gastroesophageal reflux disorder, post-operative ileus, intestinal pseudo-obstruction, drug-induced delayed transit, Barrett esophagus, intestinal pseudoileus, acute gastritis, chronic gastritis, gastric ulcer, duodenal ulcer, non-ulcer dyspepsia, Crohn's disease, celiac disease and delayed gastric emptying caused by gastric neurosis, comprising administering to a patient in need thereof, a therapeutically effective amount of the compound of formula (I), or a stereoisomer, or a pharmaceutically acceptable salt thereof.

In yet another embodiment, the present invention relates to the compound of formula (I), or a stereoisomer, or a pharmaceutically acceptable salt thereof for use in the treatment of gastrointestinal disease or disorder selected from irritable bowel syndrome, chronic constipation, functional dyspepsia, gastroparesis, gastroesophageal reflux disorder, post-operative ileus, intestinal pseudo-obstruction, drug-induced delayed transit, Barrett esophagus, intestinal pseudoileus, acute gastritis, chronic gastritis, gastric ulcer, duodenal ulcer, non-ulcer dyspepsia, Crohn's disease, celiac disease and delayed gastric emptying caused by gastric neurosis.

In yet another embodiment, the present invention relates to use of the compound of formula (I), or a stereoisomer, or a pharmaceutically acceptable salt thereof for the manufacture of a medicament for the treatment of gastrointestinal disease or disorder selected from irritable bowel syndrome, chronic constipation, functional dyspepsia, gastroparesis, gastroesophageal reflux disorder, post-operative ileus, intestinal pseudo-obstruction, drug-induced delayed transit, Barrett esophagus, intestinal pseudoileus, acute gastritis, chronic gastritis, gastric ulcer, duodenal ulcer, non-ulcer dyspepsia, Crohn's disease, celiac disease and delayed gastric emptying caused by gastric neurosis.

In embodiments, irritable bowel syndrome is selected from irritable bowel syndrome with predominant constipation, irritable bowel syndrome with predominant diarrhea, irritable bowel syndrome with mixed bowel habits, and unclassified irritable bowel syndrome.

In another embodiment, the present invention relates to the pharmaceutical composition of the compound of formula (I). In order to use the compound of formula (I), or their stereoisomers and pharmaceutically acceptable salts thereof in therapy, they will normally be formulated into a pharmaceutical composition in accordance with standard pharmaceutical practice.

The pharmaceutical compositions of the present invention may be formulated in a conventional manner using one or more pharmaceutically acceptable excipients. The pharmaceutically acceptable excipients are diluents, disintegrants, binders, lubricants, glidants, polymers, coating agents, solvents, cosolvents, preservatives, wetting agents, thickening agents, antifoaming agents, sweetening agents, flavouring agents, antioxidants, colorants, solubilizers, plasticizer, dispersing agents and the like.

In another embodiment, the pharmaceutical composition comprising the compounds of the invention may be formulated in the form of pills, tablets, coated tablets, capsules, powder, granules, pellets, patches, implants, films, liquids, semi-solids, gels, aerosols, emulsions, elixirs and the like. Such pharmaceutical compositions and processes for preparing same are well known in the art.

In another embodiment, the pharmaceutical composition of the instant invention contains 1 to 90%, 5 to 75% or 10 to 60% by weight of the compounds of the instant invention or pharmaceutically acceptable salt thereof. The amount of the active compounds or its pharmaceutically acceptable salt in the pharmaceutical composition(s) can range from about 1 mg to about 500 mg, from about 5 mg to about 400 mg, from about 5 mg to about 250 mg, from about 7 mg to about 150 mg, or in any range falling within the broader range of 1 mg to 500 mg.

The dose of the active compounds can vary depending on factors such as age and weight of patient, nature and severity of the disease to be treated and such other factors. Therefore, any reference regarding therapeutically effective amounts of the compounds of general formula (I), stereoisomers and pharmaceutically acceptable salts thereof refer to the aforementioned factors.

The following abbreviations are used herein:
5-HT: 5-Hydroxytryptamine
$5\text{-HT}_4$: 5-Hydroxytryptamine 4
ANOVA: Analysis of variance
APAP: N-acetyl-para-aminophenol
AUC: Area under the curve
$CH_3CN$: Acetonitrile
$Cs_2CO_3$: Cesium carbonate
$C_{max}$: Maximum concentration
cAMP: cyclic Adenosine monophosphate
DCM: Dichloromethane
DCC: N,N'-Dicyclohexylcarbodiimide
DIPEA: N,N-Diisopropylethylamine
DMEM: Dulbecco's Modified Eagle Medium
DMF: N,N-Dimethylformamide
DMSO: Dimethyl sulfoxide
$EC_{50}$: Half maximal effective concentration
EDC·HCl: 1-Ethyl-3-(3-dimethylaminopropyl) carbodiimide. HCl
EtOH: Ethanol
EtOAc: Ethyl Acetate
g: Grams
hERG: Human ether-a-go-go related gene
HATU: 2-(7-Aza-1H-benzotriazole-1-yl)-1,1,3,3-tetramethyluronium hexafluorophosphate
HEPES: 4-(2-hydroxyethyl)-1-piperazineethanesulfonic acid)
HEK293: Human embryonic kidney 293 cells
HOBt: 1-Hydroxybenzotriazole
$H_3PO_4$: Phosphoric acid
$HCOONH_4$: Ammonium formate
h: hour(s)
IPA HCL: Isopropanol hydrochloride
kg: Kilogram
$K_2CO_3$: Potassium carbonate
KOH: Potassium Hydroxide
LC-MS/MS: Liquid chromatography-Mass spectrometry/ Mass spectrometry
LAH: Lithium aluminium hydride
LiOH: Lithium hydroxide
min: Minutes
mg: Milligrams
mL: Milliliter
mmol: Millimole
ng: Nanogram
nM: Nanomolar
$Na_2CO_3$: Sodium carbonate
$NaHCO_3$: Sodium bicarbonate
NaOH: Sodium hydroxide
$Na_2SO_4$: Sodium sulphate
$NaBH_3CN$: Sodium cyanoborohydride
$NaBH(OAc)_3$: Sodium triacetoxyborohydride
$Pd(OH)_2$: Palladium hydroxide
p.o.: Per oral
ppm: parts per million
RT: Room Temperature
rpm: Revolutions per minute THF: Tetrahydrofuran
TBTU: 2-(1H-Benzotriazole-1-yl)-1,1,3,3-tetramethyl-aminium tetrafluoroborate
$t_{1/2}$: Half-life time
μg: Microgram
μL: Microlitre
μM: Micromolar

Intermediate 1: 1-Isopropyl-2-oxo-1,2-dihydropyrrolo[1,2-b]pyridazine-3-carboxylic acid Step 1: Acetone (69.7 mL, 1.2 mol) was added dropwise to a stirred mixture of 1-amino-1H-pyrrole-2-carboxamide (100 g, 0.8 mol) and acetic acid (48 g, 0.8 mol) in methanol (700 mL) at RT and the resulting solution was stirred for 1 h followed by the addition of NaBH$_3$CN (100.5 g, 1.59 mol) in portions at 25-30° C. and stirred for 3 h. Reaction mass was concentrated to obtain a residual mass which was diluted with cold water (1000 mL), basified with aqueous NH$_3$ (pH~9) and extracted with EtOAc (1000 mL×4). The combined organic layers were washed with brine solution (500 mL), dried over anhydrous Na$_2$SO$_4$, filtered and concentrated under vacuum to obtain crude mass which was triturated with EtOAc: n-hexane (10:90) to obtain 1-isopropylamino-1H-pyrrole-2-carboxamide. Yield: Quantitative; $^1$H-NMR (DMSO-d$_6$, 400 MHz) δ ppm: 0.91-0.92 (d, J=6.1 Hz, 6H), 4.07-4.11 (m, 1H), 5.95-5.96 (t, J=3.3 Hz, 1H), 6.68-6.69 (dd, J=1.7, 4.0 Hz, 1H), 6.95-6.97 (m, 2H), 7.09 (bs, 1H), 7.94 (bs, 1H); Mass (m/z): 168.2 (M+H)$^+$.

Step 2: KOH flakes (715 g, 12.76 mol) were added in portions to a stirred mixture of 1-isopropylamino-1H-pyrrole-2-carboxamide (step 1, 133 g, 0.79 mol) in methanol: water (200 mL: 800 mL) and then refluxed for 20 h. The reaction mixture was cooled to RT and acidified it with concentrated HCl (pH~2) and was extracted with EtOAc (1000 mL×4). The combined organic layers were washed with brine solution (500 mL), dried over anhydrous Na$_2$SO$_4$, filtered and concentrated under vacuum to obtain 1-isopropylamino-1H-pyrrole-2-carboxylic acid. Yield: 120.9 g; H-NMR (DMSO-d$_6$, 400 MHz) δ ppm: 0.92-0.94 (d, J=6.3 Hz, 6H), 3.18-3.28 (m, 1H), 6.02-6.03 (t, J=3.6 Hz, 1H), 6.74-6.79 (m, 2H), 7.09-7.10 (d, J=2.0 Hz, 1H), 12.74 (bs, 1H); Mass (m/z): 169.1 (M+H)$^+$.

Step 3: DIPEA (236 mL, 1.35 mol), HOBt (100.8 g, 0.74 mol) and EDC·HCl (168.4 g, 0.88 mol) were added to a stirred solution of 1-isopropylamino-1H-pyrrole-2-carboxylic acid (114 g, 0.678 mol) in DMF (300 mL) at RT and further stirred for 2 h followed by the addition of N,O-dimethylhydroxylamine hydrochloride (79.4 g, 0.81 mol). The reaction mixture was further stirred at RT for 24 h, poured into water (2000 mL) and extracted with EtOAc (1000 mL×4). The combined organic layers were washed with brine solution (500 mL), dried over anhydrous Na$_2$SO$_4$, filtered and concentrated under vacuum to obtain crude mass which was purified by column chromatography using EtOAc: n-hexane (10:90) to obtain N-methoxy-N-methyl-1-isopropylamino-1H-pyrrole-2-carboxamide. Yield: 56.2 g; $^1$H-NMR (CDCl$_3$, 400 MHz) δ ppm: 0.99-1.00 (d, J=6.3 Hz, 6H), 3.06-3.09 (m, 1H), 3.33 (s, 3H), 3.70 (s, 3H), 5.99-6.00 (t, J=3.4 Hz, 1H), 6.91-6.92 (d, J=3.3 Hz, 2H), 6.95-6.96 (d, J=1.0 Hz, 1H); Mass (m/z): 212.1 (M+H)$^+$.

Step 4: LAH (545 mL, 0.54 mol, 1M in THF) was added dropwise to a stirred solution of N-methoxy-N-methyl-1-isopropylamino-1H-pyrrole-2-carboxamide (76.7 g, 0.36 mol) in THF (800 mL) at −20° C. to −15° C. and maintained for 1 h at this temperature. Water was added dropwise to the reaction mixture carefully at −10 to 5° C. followed by addition of EtOAc (2000 mL) and the mixture was filtered through hyflow. The organic layer was separated, washed with brine solution (250 mL), dried over anhydrous Na$_2$SO$_4$, filtered and concentrated under vacuum to obtain 1-Isopropylamino-1H-pyrrole-2-carboxaldehyde. Yield: 50.9 g; $^1$H-NMR (CDCl$_3$, 400 MHz) δ ppm: 1.03-1.04 (d, J=6.2 Hz, 6H), 3.18-3.24 (m, 1H), 6.09-6.14 (m, 2H), 6.86-6.87 (dd, J=1.6, 4.3 Hz, 1H), 7.01 (s, 1H), 9.52 (s, 1H); Mass (m/z): 153.1 (M+H)$^+$.

Step 5: A stirred solution of 1-isopropylamino-1H-pyrrole-2-carboxaldehyde (54.3 g, 0.35 mol), piperidine (70.5 mL, 0.71 mol) and diethylmalonate (109 mL, 0.71 mol) in o-xylene (200 mL) was heated at 120° C. for 22 h. The reaction mixture was cooled to RT, diluted with water (1000 mL) and was extracted with EtOAc (1000 mL×3). The combined organic layers were washed with brine solution (500 mL), dried over anhydrous Na$_2$SO$_4$, filtered and concentrated under vacuum to obtain crude mass which was purified by column chromatography using methanol: DCM (1:99) to obtain ethyl 1-isopropyl-2-oxo-1,2-dihydropyrrolo[1,2-b]pyridazine-3-carboxylate. Yield: 79 g; $^1$H-NMR (DMSO-d$_6$, 400 MHz) δ ppm: 1.25-1.28 (t, J=7.1 Hz, 3H), 1.49-1.51 (d, J=7.7 Hz, 6H), 4.18-4.23 (q, 2H), 5.31 (m, 1H), 6.59-6.60 (dd, J=2.9, 4.1 Hz, 1H), 6.78-6.79 (d, J=4.0 Hz, 1H), 7.98 (s, 1H), 8.26 (s, 1H); Mass (m/z): 249.2 (M+H)$^+$.

Step 6: LiOH·H$_2$O (23.2 g, 0.553 mol) in 125 mL of water was added in portions to a stirred solution of ethyl 1-isopropyl-2-oxo-1,2-dihydropyrrolo[1,2-b]pyridazine-3-carboxylate (68.7 g, 0.27 mol) in THF (500 mL) at 0° C. The resulting mass was stirred for 2 h at RT. The reaction mixture was concentrated under vacuum to remove excess THF, 500 mL of cold water was added to the mass and acidified with dilute HCl (pH-2) during which solids were precipitated. These solids were filtered and dissolved in DCM (500 mL). The organic layer was washed with brine solution (250 mL), dried over anhydrous Na$_2$SO$_4$, filtered and concentrated under vacuum to obtain title compound. Yield: 56.3 g; $^1$H-NMR (DMSO-d$_6$, 400 MHz) δ ppm: 1.59-1.60 (d, J=6.4 Hz, 6H), 5.44 (s, 1H), 6.77-6.78 (dd, J=2.9, 4.3 Hz, 1H), 7.00-7.02 (d, J=4.2 Hz, 1H), 8.20 (s, 1H), 8.60 (s, 1H), 14.08 (s, 1H); Mass (m/z): 221.1 (M+H)$^+$.

Intermediate 2: Ethyl 4-hydroxy-1-isopropyl-2-oxo-1,2-dihydropyrrolo[1,2-b]pyridazine-3-carboxylate Step 1: Triphosgene (200 g, 0.67 mol) was added in portions to a stirred solution of 1-isopropylamino-1H-pyrrole-2-carboxylic acid (intermediate 1 step 2, 113.7 g, 0.67 mol) in a mixture of DMF (10.4 mL, 0.13 mol) and DCM (1000 mL) under nitrogen atmosphere at 0-5° C. and the reaction mixture was stirred to 25° C. for 48 h. The reaction mixture was diluted with DCM (1500 mL), was washed with aqueous NaHCO$_3$ (1000 mL), washed with water (500 mL), brine solution (500 mL), dried over Na$_2$SO$_4$ and concentrated under vacuum to obtain 4-isopropyl-6-oxa-3a,4-diazaindene-5,7-dione. Yield: 91 g; $^1$H-NMR (CDCl$_3$, 400 MHz) δ ppm: 1.03-1.05 (d, J=6.7 Hz, 3H), 1.29-1.31 (d, J=6.6 Hz, 3H), 4.66-4.73 (m, 1H), 6.32-6.36 (m, 1H), 6.99-7.00 (m, 1H), 7.33-7.35 (m, 1H); Mass (m/z): 195.2.

Step 2: A solution of diethyl malonate (375 g, 2.34 mol) in DMF (100 mL) was added to a stirred suspension of sodium hydride (37 g, 0.93 mol; 60% dispersion in mineral oil) in DMF (100 mL) under nitrogen atmosphere at 0-5° C. and then stirred at RT for 1 h followed by the addition of a solution of 4-isopropyl-6-oxa-3a,4-diazaindene-5,7-dione (91 g, 0.46 mol). The reaction mixture was heated to 120° C., maintained for 15 h, cooled to 0-5° C., acidified with concentrated HCl (pH~2) and extracted with EtOAc (1000 mL×3). The combined organic layers were washed with brine solution (500 mL), dried over $Na_2SO_4$ and concentrated under vacuum to get crude compound which was purified by column chromatography using DCM: n-hexane (50:50) to obtain title compound.

Yield: 42 g; $^1$H-NMR ($CDCl_3$, 400 MHz) δ ppm: 1.41-1.48 (t, J=7.1 Hz, 3H), 1.56-1.57 (d, J=7.1 Hz, 6H), 4.26-4.48 (m, 2H), 5.56-5.59 (m, 1H), 6.49-6.51 (m, 1H), 6.91-6.92 (m, 1H), 7.36 (s, 1H), 14.08 (s, 1H); Mass (m/z): 265.2 $(M+H)^+$.

Intermediate 3: tert-Butyl 3-amino-8-azabicyclo [3.2.1]octane-8-carboxylate tert-Butyl 3-oxo-8-azabicyclo[3.2.1]octane-8-carboxylate [CAS: 185099-67-6](60 g, 0.26 mol) was added to a stirred suspension of Pd/C (30 g) and $HCOONH_4$ (336 g, 5.33 mol) in methanol: water (840 mL:120 mL) at RT and resulting mass was stirred for 48 h. The reaction mixture was filtered through a hyflow and the filtrate was concentrated under vacuum to obtain a residual solid mass which was diluted with cold water (1000 mL), acidified with 1M $H_3PO_4$ and washed with DCM (200 mL×3). The aqueous layer was separated, basified with lye solution (pH-12) and extracted with DCM (1000 mL×3). The combined organic layers were washed with brine solution (250 mL), dried over anhydrous $Na_2SO_4$, filtered and concentrated under vacuum to obtain title compound.

Yield: 47.2 g; $^1$H-NMR ($CDCl_3$, 400 MHz) δ ppm: 1.31 (bs, 2H), 1.40-1.42 (m, 2H), 1.44 (s, 9H), 1.94-1.95 (m, 2H), 2.07-2.15 (m, 4H), 3.29-3.32 (t, J=6.0 Hz, 1H), 4.12-4.20 (broad d, 2H); Mass (m/z): 227.2 $(M+H)^+$.

Intermediate 4: (S)—N-Methyl-N-oxiranylmethyl-methanesulfonamide

A solution of N-methylmethanesulfonamide (20 g, 0.18 mol) in water (50 mL) was added dropwise to a stirred solution of NaOH (7.3 g, 0.18 mol) in water (200 mL) at 0-5° C., stirred for 1 h, followed by the addition of (S)-(+)-epichlorohydrin [CAS 67843-74-7](33.9 g, 0.36 mol) at 0-5° C. The reaction mixture was further stirred for 20 h at 0-5° C., diluted with DCM (450 mL), stirred for 1 h at 0 to 5° C., washed with 1 M $H_3PO_4$ (170 mL). The organic layer was separated, washed with brine solution (25 mL), dried over anhydrous $Na_2SO_4$, filtered and concentrated under vacuum to obtain title compound. Yield: 10 g; Mass (m/z): 166.2 $(M+H)^+$.

Intermediate 5: (R)—N-Methyl-N-oxiranylmethyl-methanesulfonamide

A solution of N-methylmethanesulfonamide (3 g, 0.027 mol) in water (7.5 mL) was added drop wise to a stirred solution of NaOH (1.1 g, 0.027 mol) in water (15 mL) at 0-5° C., stirred for 1 h, followed by the addition of (R)-(−)-epichlorohydrin [CAS 51594-55-9](5 g, 0.054 mol) at 0-5° C. The reaction mixture was further stirred for 20 h at 0-5° C., diluted with DCM (50 mL), stirred for 20 min at 0-5° C., washed with 1 M $H_3PO_4$ (25 mL). The organic layer was separated, washed with brine solution (25 mL), dried over anhydrous $Na_2SO_4$, filtered and concentrated under vacuum to obtain title compound. Yield: 2.5 g; Mass (m/z): 166.2 $(M+H)^+$.

Intermediate 6: N-Methyl-N-oxiranylmethylmethanesulfonamide

A solution of N-methylmethanesulfonamide (6 g, 0.055 mol) in water (15 mL) was added dropwise to a stirred solution of NaOH (2.2 g, 0.055 mol) in water (30 mL) at 0-5° C., stirred for 1 h, followed by the addition of racemic-epichlorohydrin (10.1 g, 0.11 mol) at 0-5° C. The reaction mixture was further stirred for 20 h at 0-5° C., diluted with DCM (100 mL), stirred for 30 min at 0-5° C., washed with 1 M $H_3PO_4$ (50 mL). The organic layer was separated, washed with brine solution (50 mL), dried over anhydrous $Na_2SO_4$, filtered and concentrated under vacuum to obtain title compound. Yield: 4.6 g; Mass (m/z): 166.2 $(M+H)^+$.

Intermediate 7: (S)—N-Oxiranylmethylmethanesulfonamide

Using a similar procedure as given in the preparation of intermediate 4 and methanesulfonamide, intermediate 7 was prepared. Yield: 0.6 g; Mass (m/z): 152.2 $(M+H)^+$.

Intermediate 8: (S)—N-Methyl-N-oxiranylmethylacetamide

Using a similar procedure as given in the preparation of intermediate 4 and N-methylacetamide, intermediate 8 was prepared. Yield: 0.9 g; Mass (m/z): 130.2 $(M+H)^+$.

Intermediate 9: (S)-1-Methanesulfonyl-4-oxiranylmethylpiperazine

Using a similar procedure as given in the preparation of intermediate 4 and 1-methanesulfonylpiperazine, intermediate 9 was prepared. Yield: 0.8 g; Mass (m/z): 221.3 $(M+H)^+$.

Intermediate 10: 1-{4-[2-(3-Amino-8-azabicyclo [3.2.1]oct-8-yl) ethyl]piperazin-1-yl} ethanone Step 1: A mixture of benzaldehyde (2 g, 0.018 mol) and tert-butyl 3-amino-8-aza-bicyclo[3.2.1]octane-8-carboxylate (5.1 g, 0.022 mol) in DCM (100 mL) was stirred for 3 h followed by addition of $NaBH(OAc)_3$ (5.9 g, 0.028 mol) in three equal lots, each in 15 min time interval and the reaction mixture was stirred for 18 h at RT. The reaction mixture was poured into water (100 mL), basified with aqueous $NH_3$ (pH~9) and extracted with DCM (100 mL×3). The combined organic extracts were washed with brine solution (50 mL), dried over anhydrous $Na_2SO_4$, filtered and concentrated under vacuum to obtain crude mass which was purified by column chromatography using EtOAc: n-hexane (5:95) to obtain tert-butyl 3-dibenzylamino-8-azabicyclo [3.2.1]octane-8-carboxylate. Yield: 6.1 g; $^1$H-NMR (DMSO-$d_6$, 400 MHz) δ ppm: 1.23 (s, 9H), 1.33-1.40 (m, 2H), 1.51-1.60 (m, 4H), 1.97-1.99 (m, 2H), 2.29-2.36 (m, 1H), 2.44-2.46 (m, 1H), 2.70-2.78 (m, 1H), 3.58 (s, 2H), 3.60 (s, 2H), 7.16-7.34 (m, 10H); Mass (m/z): 407.3 $(M+H)^+$.

Step 2: EtOH·HCl (12 mL) was added dropwise to a stirred solution of tert-butyl 3-dibenzylamino-8-azabicyclo [3.2.1]octane-8-carboxylate (6 g, 0.014 mol) in DCM (300 mL) at 0-5° C. and the resulting mixture was stirred for overnight at RT. The reaction mass was concentrated to obtain a syrupy mass which was diluted with cold water (50 mL), basified with aqueous $NH_3$ (pH~9) and extracted with DCM (100 mL×3). The combined organic extracts were washed with brine solution (25 mL), dried over anhydrous Na$_2$SO$_4$, filtered and concentrated under vacuum to obtain (8-azabicyclo[3.2.1]oct-3-yl)dibenzylamine. Yield: 4.4 g; $^1$H-NMR (DMSO-d$_6$, 400 MHz) δ ppm: 1.13-1.19 (m, 2H), 1.48-1.59 (m, 4H), 2.03-2.11 (m, 2H), 2.49 (s, 1H), 2.50-2.51 (m, 2H), 2.86-2.91 (m, 1H), 3.49 (s, 4H), 7.16-7.32 (m, 10H); Mass (m/z): 307.3 (M+H)$^+$.

Step 3: K$_2$CO$_3$ (1.44 g, 0.01 mol) was added in portions to a stirred solution of (8-azabicyclo[3.2.1]oct-3-yl) dibenzylamine (1.6 g, 0.005 mol) and tert-butyl 4-(2-chloro acetyl) piperazin-1-carboxylate [CAS 190001-40-2](1.23 g, 0.004 mol) in CH$_3$CN (40 mL) at RT and the resulting mixture was refluxed for 5 h, then cooled to RT and poured into water (100 mL) and was extracted with EtOAc (100 mL×3). The combined organic extracts were washed with brine solution (25 mL), dried over anhydrous Na$_2$SO$_4$, filtered and concentrated under vacuum to obtain crude mass which was purified by column chromatography using EtOAc: n-hexane (2:98) to obtain tert-butyl4-[2-(3-dibenzylamino-8-aza bicyclo[3.2.1]oct-8-yl) acetyl]piperazine-1-carboxylate. Yield: 2.19 g; Mass (m/z): 533.5 (M+H)$^+$.

Step 4: EtOH·HCl (20 mL) was added dropwise to a stirred solution of tert-butyl 4-[2-(3-dibenzylamino-8-azabicyclo[3.2.1]oct-8-yl)acetyl]piperazin-1-carboxylate (2.1 g, 0.003 mol) in DCM (300 mL) at 0-5° C. and the resulting mixture was stirred for overnight at RT. The reaction mass was concentrated to obtain a syrupy mass which was diluted with cold water (50 mL), basified with aqueous NH$_3$ (pH~9) and extracted with DCM (100 mL×3). The combined organic extracts were washed with brine solution (25 mL), dried over anhydrous Na$_2$SO$_4$, filtered and concentrated under vacuum to obtain 2-(3-dibenzylamino-8-azabicyclo [3.2.1]oct-8-yl)-1-piperazin-1-yl ethanone. Yield: 1.55 g; H-NMR (DMSO-d$_6$, 400 MHz) δ ppm: 1.21-1.22 (m, 3H), 1.46-1.48 (m, 2H), 1.91-1.93 (m, 4H), 2.12-2.21 (m, 4H), 2.53-2.57 (m, 2H), 2.70-2.72 (m, 1H), 2.87-2.97 (m, 4H), 3.14 (bs, 2H), 3.49 (s, 4H), 7.18-7.30 (m, 10H); Mass (m/z): 433.5 (M+H)$^+$.

Step 5: LAH solution (5.2 mL, 0.005 mol, 1M in THF) was added dropwise to a stirred solution of 2-(3-dibenzylamino-8-azabicyclo[3.2.1]oct-8-yl)-1-piperazin-1-yl ethanone (1.5 g, 0.003 mol) in THF (30 mL) at 0-5° C. and the resulting mixture was stirred further for 1 h at the same temperature. Cold water (10 mL) was added dropwise to the above reaction mixture carefully followed by the addition of EtOAc (50 mL) and the mixture was filtered through a hyflow. The organic layer was separated, washed with brine solution (25 mL), dried over anhydrous Na$_2$SO$_4$, filtered and concentrated under vacuum to obtain {8-[2-(piperazin-1-yl) ethyl]-8-azabicyclo[3.2.1]oct-3-yl}dibenzylamine. Yield: 1.20 g; Mass (m/z): 419.5 (M+H)$^+$.

Step 6: Acetyl chloride (0.2 mL, 0.0024 mol) was added dropwise to a stirred solution of {8-[2-(piperazin-1-yl) ethyl]-8-azabicyclo[3.2.1]oct-3-yl} dibenzylamine (1.2 g, 0.002 mol) and triethylamine (0.6 mL, 0.004 mol) in DCM (30 mL) at 0-5° C. and the resulting mixture was stirred for 1 h at RT. The reaction mixture was poured into water (50 mL) and was extracted with DCM (50 mL×3). The combined organic extracts were washed with brine solution (25 mL), dried over anhydrous Na$_2$SO$_4$, filtered and concentrated under vacuum to obtain a crude mass which was purified by column chromatography using methanol: chloroform (10:90) to obtain 1-{4-[2-(3-dibenzylamino-8-azabicyclo[3.2.1]oct-8-yl)ethyl]piperazin-1-yl}ethanone.

Yield: 0.75 g; Mass (m/z): 461.4 (M+H)$^+$.

Step 7: A mixture of 1-{4-[2-(3-dibenzylamino-8-azabicyclo[3.2.1]oct-8-yl)ethyl]piperazin-1-yl}ethanone (0.7 g, 1.52 mmol) and Pd(OH)$_2$ on carbon (0.7 g) in methanol (10 mL) was stirred under hydrogen gas balloon for 20 h and the reaction mixture was filtered through a hyflow. The filtrate was concentrated under vacuum to obtain title compound. Yield: 467 mg; H-NMR (CDCl$_3$, 400 MHz) δ ppm: 1.40-1.42 (m, 2H), 1.57-1.61 (m, 2H), 2.01-2.12 (m, 5H), 2.38-2.47 (m, 2H), 2.57-2.59 (m, 4H), 2.78-2.80 (m, 2H), 2.95-2.97 (m, 4H), 3.46-3.60 (m, 5H), 3.81-3.97 (m, 2H); Mass (m/z): 281.3 (M+H)$^+$.

Intermediate 11:
N-(3-Bromo-propyl)-methanesulfonamide

Mesyl chloride (0.39 mL, 0.0045 mol) was added dropwise to a stirred solution of 3-bromo-propylaminehydrobromide (1 g, 0.0045 mol) and triethylamine (1.86 mL, 0.013 mol) in DCM (30 mL) at 0-10° C. and the resulting mixture was stirred for 3 h at RT. The reaction mixture was poured into water (50 mL) and was extracted with DCM (50 mL×3). The combined organic extracts were washed with brine solution (25 mL), dried over anhydrous Na$_2$SO$_4$, filtered and concentrated under vacuum to obtain title compound. Yield: 0.93 g; Mass (m/z): 217.1, 219.2 (M+H)$^+$.

Intermediate 12: N-(3-Bromopropyl) isopropylsulfonamide

Using a similar procedure as given in the preparation of intermediate 11, and isopropylsulfonyl chloride, intermediate 12 was prepared. Yield: 0.7 g; Mass (m/z): 245.2, 247.1 (M+H)$^+$.

Intermediate 13:
N-(2-Bromo-ethyl)-methanesulfonamide

Using a similar procedure as given in the preparation of intermediate 11, mesyl chloride and 2-bromo-ethylamine, intermediate 13 was prepared. Yield: 0.7 g; Mass (m/z): 203.1, 205.1 (M+H)$^+$.

Intermediate 14: N-(2-Bromoethyl) isopropylsulfonamide

Using a similar procedure as given in the preparation of intermediate 11, isopropylsulfonyl chloride and 2-bromo-ethylamine, intermediate 14 was prepared. Yield: 0.5 g; Mass (m/z): 231.1, 232.2 (M+H)$^+$.

Intermediate 15: N-(3-Bromo-propyl)-acetamide

Using a similar procedure as given in the preparation of intermediate 11, and acetyl chloride, intermediate 15 was prepared. Yield: 0.7 g; Mass (m/z): 181, 183.1 (M+H)$^+$.

Intermediate 16: Methyl N-(3-bromopropyl) carbamate

Using a similar procedure as given in the preparation of intermediate 11 and methylchloroformate, intermediate 16 was prepared. Yield: 0.3 g; Mass (m/z): 197.1, 199.1 (M+H)$^+$.

Intermediate 17: (2-Bromo-ethyl)-carbamic acid methyl ester

Using a similar procedure as given in the preparation of intermediate 11, 2-bromo-ethylamine and methylchloroformate, intermediate 17 was prepared. Yield: 0.3 g; Mass (m/z): 183.1, 185.1 (M+H)$^+$.

Intermediate 18: [N-(8-Azabicyclo[3.2.1]oct-3-yl)]-1-isopropyl-2-oxo-1,2-dihydro-pyrrolo[1,2-b]pyridazine-3-carboxamide Step 1: DIPEA (47.4 mL, 0.272 mol), TBTU (35 g, 0.109 mol) and tert-butyl-3-amino-8-aza-bicyclo[3.2.1]octane-8-carboxylate (intermediate 3, 20.36 g, 0.09 mol) were added to a stirred solution of 1-isopropyl-2-oxo-1,2-dihydropyrrolo[1,2-b]pyridazine-3-carboxylic acid (intermediate 1, 20 g, 0.09 mol) in DMF (100 mL) at RT and maintained for 3 h. The reaction mixture was poured onto cold water (1000 mL) under stirring during which solids precipitated. These solids were filtered, dissolved in DCM (500 mL), was washed with brine solution (100 mL), dried over anhydrous $Na_2SO_4$, filtered and concentrated under vacuum to obtain tert-butyl-3-[(1-isopropyl-2-oxo-1,2-dihydro pyrrolo[1,2-b]pyridazine-3-carbonyl) amino]-8-aza bicyclo[3.2.1]octane-8-carboxylate. Yield: 35.1 g; $^1$H-NMR (DMSO-$d_6$, 400 MHz) δ ppm: 1.41 (s, 9H), 1.55-1.57 (d, J=6.8 Hz, 6H), 1.64-1.67 (m, 2H), 2.00-2.05 (m, 6H), 4.09 (bs, 2H), 4.17-4.19 (m, 1H), 5.51 (s, 1H), 6.64-6.66 (dd, J=2.9, 6.4 Hz, 1H), 6.85-6.86 (d, J=4.0 Hz, 1H), 8.01 (s, 1H), 8.49 (s, 1H), 10.11-10.13 (d, J=7.6 Hz, 1H); Mass (m/z): 429.3 (M+H)$^+$.

Step 2: Trifluoroacetic acid (161 mL, 2.1 mol) was added dropwise to a stirred solution of tert-butyl 3-[(1-isopropyl-2-oxo-1,2-dihydro pyrrolo[1,2-b]pyridazine-3-carbonyl) amino]-8-aza bicyclo[3.2.1]octane-8-carboxylate (30 g, 0.07 mol) in DCM (300 mL) at 0° C. and then stirred for overnight at RT. The reaction mixture was poured in to cold water (700 mL), basified with aqueous ammonia (pH~9) and extracted with DCM (500 mL×4). The combined organic layers were washed with brine solution (250 mL), dried over anhydrous $Na_2SO_4$, filtered and concentrated under vacuum to obtain title compound. Yield: 22.7 g; $^1$H-NMR (CDCl$_3$, 400 MHz) δ ppm: 1.63-1.64 (d, J=7.1 Hz, 6H), 1.82-1.85 (d, J=14.6 Hz, 2H), 1.95-1.98 (m, 2H), 2.13-2.20 (m, 4H), 2.79 (s, 1H), 3.60 (s, 2H), 4.30-4.35 (m, 1H), 5.71 (bs, 1H), 6.57-6.58 (dd, J=2.9, 4.2 Hz, 1H), 6.67-6.68 (d, J=4.0 Hz, 1H), 7.44 (s, 1H), 8.55 (s, 1H), 10.11-10.12 (d, J=7.2 Hz, 1H); Mass (m/z): 329.2 (M+H)$^+$.

Intermediate 19: N-(8-azabicyclo[3.2.1]oct-3-yl){4-hydroxy-1-isopropyl-2-oxo-1,2-dihydro pyrrolo[1,2-b]pyridazine}-3-carboxamide Step 1: $K_2CO_3$ (0.026 g, 0.18 mmol) was added in portions to a stirred solution of ethyl 4-hydroxy-1-isopropyl-2-oxo-1,2-dihydropyrrolo[1,2-b]pyridazine-3-carboxylate (intermediate 2, 0.5 g, 1.89 mmol) and tert-butyl3-amino-8-aza-bicyclo[3.2.1]octane-8-carboxylate (intermediate 3, 0.51 g, 2.27 mmol) in toluene (10 mL) at RT and then refluxed for 18 h. The reaction mixture was cooled to RT, poured in to water (25 mL) and extracted with EtOAc (50 mL×3). The combined organic extracts were washed with brine solution (25 mL), dried over anhydrous $Na_2SO_4$, filtered and concentrated under vacuum to obtain crude mass which was purified by column chromatography using EtOAc: n-hexanes (25:75) to obtain tert-butyl-3-[(4-hydroxy-1-isopropyl-2-oxo-1,2-dihydropyrrolo[1,2-b]pyridazine-3-carbonyl)amino]-8-azabicyclo[3.2.1]octane-8-carboxylate. Yield: 0.98 g; Mass (m/z): 445.3 (M+H)$^+$.

Step 2: EtOH·HCl (1.2 mL, 5 vol) was added dropwise to a stirred solution of tert-butyl-3-[(4-hydroxy-1-isopropyl-2-oxo-1,2-dihydropyrrolo[1,2-b]pyridazine-3-carbonyl) amino]-8-azabicyclo[3.2.1]octane-8-carboxylate (0.23 g, 0.52 mmol) in DCM (20 mL) at 0° C., stirred for 18 h at RT and then concentrated under vacuum to obtain a syrupy mass. This mass was diluted with water (10 mL), basified with aqueous $NH_3$ (pH~9), extracted with DCM (25 mL×3). The combined organic layers were washed with brine solution (10 mL), dried over anhydrous $Na_2SO_4$, filtered and concentrated under vacuum to obtain the title compound. Yield: 0.72 g; Mass (m/z): 345.2 (M+H)$^+$.

Example 1: (R)—N-{8-[2-Hydroxy-3-[(N-methyl)methanesulfonamido]propyl]-8-azabicyclo[3.2.1]oct-3-yl}[1-isopropyl-2-oxo-1,2-dihydro pyrrolo[1,2-b]pyridazine]-3-carboxamide

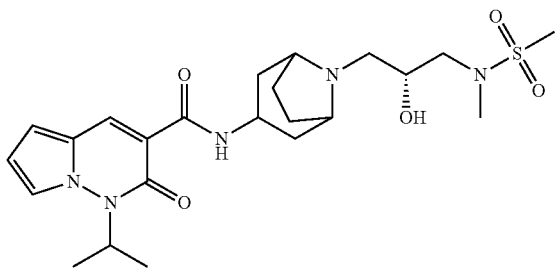 [SMILES: CC(C)n1c(=O)c(C(=O)NC2CC3CCC(C2)N3C[C@@H](O)CN(C)S(C)(=O)=O)cc2cccn21]

(S)—N-methyl-N-oxiranylmethylmethanesulfonamide (intermediate 4, 5 g, 0.03 mol) followed by DIPEA (2.65 mL, 0.015 mol) were added to a stirred solution of [N-(8-azabicyclo[3.2.1]oct-3-yl)]-1-isopropyl-2-oxo-1,2-dihydro-pyrrolo[1,2-b]pyridazine-3-carboxamide (intermediate 18, 5 g, 0.015 mol) in methanol (75 mL) at RT and the reaction mixture was heated at reflux temperature for 24 h. The reaction mixture was cooled to RT, diluted with EtOAc (500 mL), washed with water (100 mL), brine solution (25 mL), dried over anhydrous $Na_2SO_4$, filtered and concentrated under vacuum to obtain crude mass which was purified by column chromatography using methanol: DCM (1:99) to obtain the title compound. Yield: 3.75 g; $^1$H-NMR (DMSO-$d_6$, 400 MHz) δ ppm: 1.56-1.58 (d, J=6.8 Hz, 6H), 1.94-2.32 (m, 8H), 2.84 (s, 3H), 2.89 (s, 3H), 3.04-3.32 (m, 4H), 3.70 (bs, 1H), 4.10 (bs, 2H), 4.70 (bs, 1H), 5.53 (bs, 1H), 5.75 (bs, 1H), 6.65 (s, 1H), 6.85 (s, 1H), 8.01 (s, 1H), 8.48 (s, 1H), 10.02 (bs, 1H); Mass (m/z): 494.4 (M+H)$^+$.

Example 2: (R)—N-{8-[2-Hydroxy-3-[(N-methyl)methanesulfonamido]propyl]-8-azabicyclo[3.2.1]oct-3-yl}[1-isopropyl-2-oxo-1,2-dihydro pyrrolo[1,2-b]pyridazine]-3-carboxamide L-(+)-tartrate

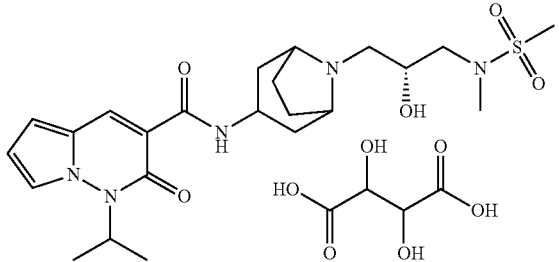

L-(+)-tartaric acid (1.11 g, 0.007 mol) was added to a stirred solution of (R)—N-{8-[2-hydroxy-3-[(N-methyl)methanesulfonamido]propyl]-8-azabicyclo[3.2.1]oct-3-yl}[1-isopropyl-2-oxo-1,2-dihydro pyrrolo[1,2-b]pyridazine]-

3-carboxamide (Example 1, 3.7 g, 0.007 mol) in DCM: methanol (30:10) under nitrogen atmosphere and stirred further at RT for 2 h and concentrated under vacuum to obtain title compound. Yield: 4.73 g; $^1$H-NMR (CD$_3$OD, 400 MHz) δ ppm: 1.66-1.68 (d, J=6.9 Hz, 6H), 2.15-2.19 (m, 2H), 2.48-2.49 (m, 4H), 2.59-2.60 (m, 2H), 2.91 (s, 3H), 2.99 (s, 3H), 3.10-3.20 (m, 1H), 3.24-3.25 (m, 2H), 4.12 (bs, 1H), 4.26-4.30 (m, 3H), 4.47 (s, 2H), 5.56 (bs, 1H), 6.69-6.71 (dd, J=2.9, 4.1 Hz, 1H), 6.85-6.86 (d, J=4.1 Hz, 1H), 7.89 (s, 1H), 8.52 (s, 1H), 10.64-10.66 (d, J=6.9 Hz, 1H); Mass (m/z): 494.4 (M+H)$^+$.

The following examples 3 to 20 were prepared by using the procedure as described for example 1 and example 2 with some non-critical variations using suitable intermediates.

| Example No. | Chemical structure and IUPAC Name | Characterization Data |
|---|---|---|
| 3 | 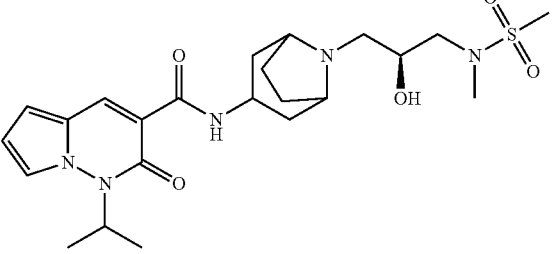<br>(S)-N-{8-[4-Hydroxy-3-[(N-methyl)methanesulfonamido]propyl]-8-azabicyclo[3.2.1]oct-3-yl} [1-isopropyl-2-oxo-1,2-dihydropyrrolo[1,2-b]pyridazine]-3-carboxamide | Yield: 4.73 g; $^1$H-NMR (DMSO-d$_6$, 400 MHz) δ ppm: 1.55-1.57 (d, J = 6.8 Hz, 6H), 1.89-2.08 (m, 6H), 2.29-2.32 (m, 2H), 2.83 (s, 3H), 2.87 (s, 3H), 2.96-3.02 (m, 2H), 3.18-3.22 (m, 4H), 3.70-3.71 (m, 1H), 4.04-4.08 (m, 1H), 4.71 (bs, 1H), 5.53 (bs, 1H), 6.63-6.64 (dd, J = 3.2 Hz, 4 Hz, 1H), 6.85-6.85 (d, J = 4.4 Hz, 1H), 7.99 (s, 1H), 8.47 (s, 1H), 9.98-10.00 (d, J = 8.0 Hz, 1H); Mass (m/z): 494.4 (M + H)$^+$. |
| 4 | 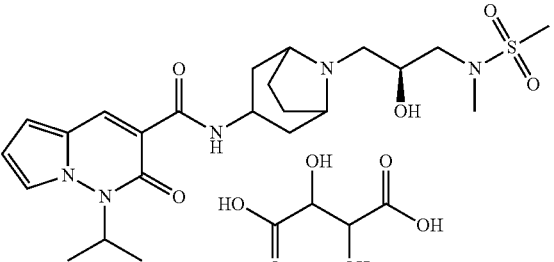<br>(S)-N-{8-[2-Hydroxy-3-[(N-methyl)methanesulfonamido]propyl]-8-azabicyclo[3.2.1]oct-3-yl} [1-isopropyl-2-oxo-1,2-dihydropyrrolo[1,2-b]pyridazine]-3-carboxamide L(+)-tartarate | Yield: 5.2 g; $^1$H-NMR (CD$_3$OD, 400 MHz) δ ppm: 1.67-1.68 (d, J = 6.8 Hz, 6H), 2.11-2.14 (m, 2H), 2.44-2.60 (m, 4H), 2.91 (s, 3H), 2.99 (s, 3H), 3.07-3.13 (m, 1H), 3.20-3.25 (m, 4H), 4.07 (bs, 1H), 4.21-4.28 (m, 3H), .4.40 (s, 2H), 5.56 (bs, 1H), 6.70 (s, 1H), 6.85-6.86 (d, J = 3.2 Hz, 1H), 7.89 (s, 1H), 8.52 (s, 1H), 10.64-10.65 (d, J = 6.4 Hz, 1H); Mass (m/z): 494.4 (M + H)$^+$. |
| 5 | 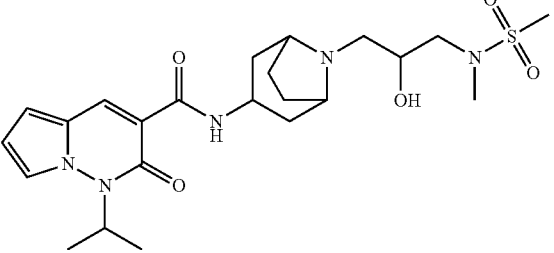<br>Racemic-N-{8-[2-Hydroxy-3-[(N-methyl)methanesulfonamido]propyl]-8-azabicyclo[3.2.1]oct-3-yl} [1-isopropyl-2-oxo-1,2-dihydropyrrolo[1,2-b]pyridazine]-3-carboxamide | Yield: 4.3 g; $^1$H-NMR (DMSO-d$_6$, 400 MHz) δ ppm: 1.55-1.57 (d, J = 7.2 Hz, 6H), 1.92-2.08 (m, 6H), 2.29-2.32 (m, 2H), 2.83 (s, 3H), 2.87 (s, 3H), 2.96-3.02 (m, 2H), 3.21-3.22 (m, 4H), 3.69-3.70 (m, 1H), 4.06-4.09 (m, 1H), 4.71 (bs, 1H), 5.53 (bs, 1H), 6.63-6.65 (dd, J = 2.8 Hz, 4 Hz, 1H), 6.84-6.85 (d, J = 4 Hz, 1H), 7.99 (s, 1H), 8.47 (s, 1H), 9.98-10.00 (d, J = 7.6 Hz, 1H); Mass (m/z): 494.4 (M + H)$^+$. |

| Example No. | Chemical structure and IUPAC Name | Characterization Data |
|---|---|---|
| 6 | 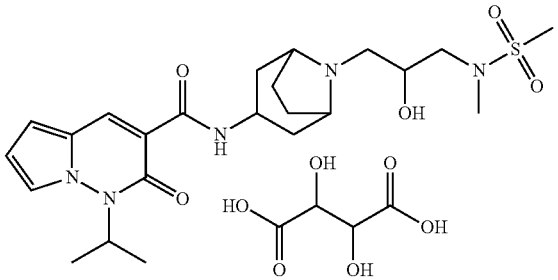<br>Racemic-N-{8-[2-Hydroxy-3-[(N-methyl)methanesulfonamido]propyl]-8-azabicyclo[3.2.1]oct-3-yl} [1-isopropyl-2-oxo-1,2-dihydro pyrrolo[1,2-b]pyridazine]-3-carboxamide L(+)-tartarate | Yield: 4.9 g; $^1$H-NMR (CD$_3$OD, 400 MHz) δ ppm: 1.67-1.68 (d, J = 6.8 Hz, 6H), 2.13-2.19 (m, 2H), 2.40-2.61 (m, 4H), 2.92 (s, 3H), 3.00 (s, 3H), 3.10-3.16 (m, 1H), 3.24-3.26 (m, 4H), 4.11 (bs, 1H), 4.24-4.30 (m, 3H), 4.43 (s, 2H), 5.57 (bs, 1H), 6.70-6.72 (dd, J = 2.8 Hz, 4 Hz, 1H), 6.85-6.87 (d, J = 4.4 Hz, 1H), 7.89 (s, 1H), 8.53 (s, 1H), 10.65-10.67 (d, J = 6.8 Hz, 1H); Mass (m/z): 494.4 (M + H)$^+$. |
| 7 | 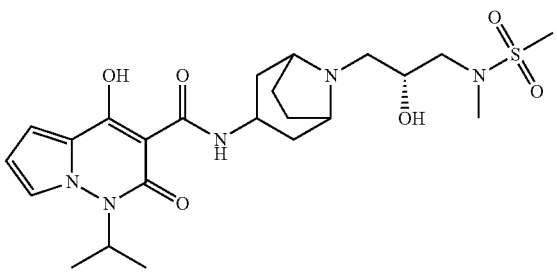 [SMILES: CC(C)n1c(=O)c(C(=O)NC2CC3CCC(C2)N3C[C@@H](O)CN(C)S(C)(=O)=O)c(O)c2cccn21]<br>(R)-N-{8-[2-Hydroxy-3-[(N-methyl)methanesulfonamido]propyl]-8-azabicyclo[3.2.1]oct-3-yl} [4-hydroxy-1-isopropyl-2-oxo-1,2-dihydro pyrrolo[1,2-b]pyridazine]-3-carboxamide | Yield: 0.5 g; $^1$H-NMR (DMSO-d$_6$, 400 MHz) δ ppm: 1.51-1.53 (d, J = 6.9 Hz, 6H), 1.78-2.38 (m, 9H), 2.84 (s, 3H), 2.90 (s, 3H), 2.98-3.14 (m, 3H), 4.03-4.15 (m, 4H), 5.32-5.44 (m, 1H), 5.74-5.82 (m, 1H), 6.59 (s, 1H), 6.87 (s, 1H), 7.94 (s, 1H), 10.56 (bs, 1H), 16.90 (bs, 1H); Mass (m/z): 510.4 (M + H)$^+$. |
| 8 | 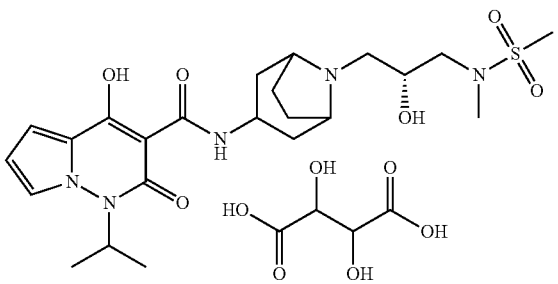<br>(R)-N-{8-[2-Hydroxy-3-[(N-methyl)methanesulfonamido]propyl]-8-azabicyclo[3.2.1]oct-3-yl} [4-hydroxy-1-isopropyl-2-oxo-1,2-dihydro pyrrolo[1,2-b]pyridazine]-3-carboxamide L-(+)-tartarate | Yield: 0.7 g; $^1$H-NMR (CD$_3$OD, 400 MHz) δ ppm: 1.61-1.63 (d, J = 7.0 Hz, 6H), 2.03-2.19 (m, 2H), 2.44-2.48 (m, 4H), 2.56-2.59 (m, 2H), 2.90 (s, 3H), 2.91-2.95 (m, 2H), 2.99 (s, 3H), 3.03-3.13 (m, 2H), 4.08-4.14 (m, 1H), 4.25-4.31 (m, 3H), 4.50 (s, 2H), 5.49-5.56 (m, 1H), 6.59-6.60 (t, J = 3.1, 6.5 Hz, 1H), 6.90-6.91 (d, J = 3.5 Hz, 1H), 7.76 (s, 1H), 10.80 (bs, 1H); Mass (m/z): 510.4 (M + H)$^+$. |
| 9 | 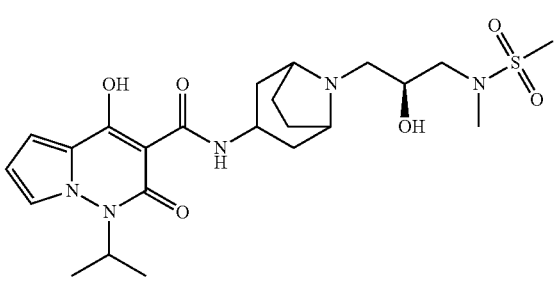 [SMILES: CC(C)n1c(=O)c(C(=O)NC2CC3CCC(C2)N3C[C@H](O)CN(C)S(C)(=O)=O)c(O)c2cccn21] | Yield: 0.17 g; $^1$H-NMR (DMSO-d$_6$, 400 MHz) δ ppm: 1.51-1.53 (d, J = 6.9 Hz, 6H), 1.78-2.08 (m, 6H), 2.28-2.32 (m, 3H), 2.84 (s, 3H), 2.90 (s, 3H), 2.98-3.12 (m, 3H), 4.02-4.14 (m, 4H), 5.32-5.44 (m, 1H), 5.74-5.82 (m, 1H), 6.69 (s, 1H), 6.87 (s, 1H), 7.99 (s, 1H), 10.56 (bs, 1H), 16.90 (bs, 1H); Mass (m/z): 510.4 (M + H)$^+$. |

| Example No. | Chemical structure and IUPAC Name | Characterization Data |
|---|---|---|
| | (S)-N-{8-[2-Hydroxy-3-[(N-methyl)methanesulfonamido]propyl]-8-azabicyclo[3.2.1]oct-3-yl} [4-hydroxy-1-isopropyl-2-oxo-1,2-dihydro pyrrolo[1,2-b]pyridazine]-3-carboxamide | |
| 10 | (S)-N-{8-[2-Hydroxy-3-[(N-methyl)methanesulfonamido]propyl]-8-azabicyclo[3.2.1]oct-3-yl} [4-hydroxy-1-isopropyl-2-oxo-1,2-dihydro pyrrolo[1,2-b]pyridazine]-3-carboxamide L-(+)-tartarate | Yield: 0.19 g; $^1$H-NMR (CD$_3$OD, 400 MHz) δ ppm: 1.61-1.63 (d, J = 7.0 Hz, 6H), 2.03-2.19 (m, 2H), 2.44-2.48 (m, 4H), 2.56-2.59 (m, 2H), 2.89 (s, 3H), 2.91-2.95 (m, 2H), 2.99 (s, 3H), 3.03-3.13 (m, 2H), 4.08-4.14 (m, 1H), 4.25-4.31 (m, 3H), 4.50 (s, 2H), 5.49-5.56 (m, 1H), 6.58-6.62 (d, J = 6.5 Hz, 1H), 6.91 (s, 1H), 7.98 (s, 1H), 10.80 (bs, 1H); Mass (m/z): 510.4 (M + H)$^+$. |
| 11 | Racemic-N-{8-[2-Hydroxy-3-[(N-methyl)methanesulfonamido]propyl]-8-azabicyclo[3.2.1]oct-3-yl} [4-hydroxy-1-isopropyl-2-oxo-1,2-dihydro pyrrolo[1,2-b]pyridazine]-3-carboxamide | Yield: 0.28 g; $^1$H-NMR (DMSO-d$_6$, 400 MHz) δ ppm: 1.51-1.53 (d, J = 6.9 Hz, 6H), 1.80-2.38 (m, 9H), 2.86 (s, 3H), 2.90 (s, 3H), 3.02-3.14 (m, 3H), 4.04-4.14 (m, 4H), 5.30-5.42 (m, 1H), 5.62-5.80 (m, 1H), 6.62 (s, 1H), 6.87 (s, 1H), 7.09 (s, 1H), 10.05 (bs, 1H), 16.91 (bs, 1H); Mass (m/z): 510.4 (M + H)$^+$. |
| 12 | Racemic-N-{8-[2-Hydroxy-3-[(N-methyl)methanesulfonamido]propyl]-8-azabicyclo[3.2.1]oct-3-yl} [4-hydroxy-1-isopropyl-2-oxo-1,2-dihydro pyrrolo[1,2-b]pyridazine]-3-carboxamide L-(+)-tartarate | Yield: 0.29 g; $^1$H-NMR (CD$_3$OD, 400 MHz) δ ppm: 1.61-1.64 (d, J = 6.9 Hz, 6H), 2.02-2.20 (m, 2H), 2.42-2.48 (m, 4H), 2.56-2.58 (m, 2H), 2.90 (s, 3H), 2.91-2.95 (m, 2H), 2.99 (s, 3H), 3.04-3.13 (m, 2H), 4.08-4.14 (m, 1H), 4.25-4.31 (m, 3H), 4.50 (s, 2H), 5.48-5.56 (m, 1H), 6.62-6.66 (s, 1H), 6.96 (s, 1H), 7.89 (s, 1H), 10.80 (bs, 1H); Mass (m/z): 510.4 (M + H)$^+$. |

-continued

| Example No. | Chemical structure and IUPAC Name | Characterization Data |
|---|---|---|
| 13 | 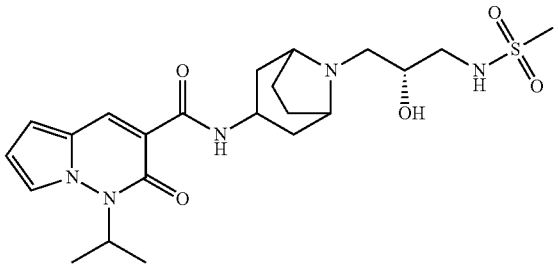 [SMILES: CC(C)n1c(=O)c(C(=O)NC2CC3CCC(C2)N3C[C@@H](O)CNS(C)(=O)=O)cc2cccn21]<br>(R)-N-{8-[2-Hydroxy-3-(methanesulfonamido)propyl]-8-azabicyclo[3.2.1]oct-3-yl} [1-isopropyl-2-oxo-1,2-dihydro pyrrolo[1,2-b]pyridazine]-3-carboxamide | Yield: 0.47 g; $^1$H-NMR (CDCl$_3$, 400 MHz) δ ppm: 1.63-1.65 (d, J = 7.1 Hz, 6H), 1.81-1.95 (m, 2H), 2.00-2.08 (m, 4H), 2.10-2.11 (m, 2H), 2.27-2.33 (m, 2H), 2.51-2.55 (m, 1H), 2.99 (s, 3H), 3.04-3.08 (m, 1H), 3.19-3.25 (m, 2H), 3.31-3.35 (m, 1H), 3.52-3.62 (m, 1H), 3.74-3.77 (m, 1H), 4.24-4.29 (m, 1H), 5.60-5.82 (bs, 1H), 6.58-6.60 (m, 1H), 6.68-6.69 (m, 1H), 7.45 (s, 1H), 8.56 (s, 1H), 10.07-10.04 (d, J = 7.3 Hz, 1H); Mass (m/z): 480.2 (M + H)$^+$. |
| 14 | 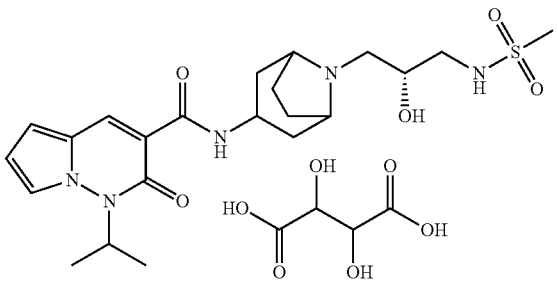<br>(R)-N-{8-[2-Hydroxy-3-(methanesulfonamido)propyl]-8-azabicyclo[3.2.1]oct-3-yl} [1-isopropyl-2-oxo-1,2-dihydro pyrrolo[1,2-b]pyridazine]-3-carboxamide L-(+)-tartarate | Yield: 0.4 g; $^1$H-NMR (CD$_3$OD, 400 MHz) δ ppm: 1.66-1.68 (d, J = 7.0 Hz, 6H), 2.10-2.18 (m, 2H), 2.37-2.47 (m, 4H), 2.56-2.60 (m, 2H), 3.00 (s, 3H), 3.14 (m, 2H), 3.19-3.21 (m, 3H), 4.12 (bs, 1H), 4.26-4.30 (m, 3H), 4.28 (m, 1H), 4.40 (s, 2H), 5.56 (bs, 1H), 6.69-6.71 (m, 1H), 6.85-6.86 (d, J = 4.2 Hz, 1H), 7.89 (s, 1H); Mass (m/z): 480.3 (M + H)$^+$. |
| 15 | 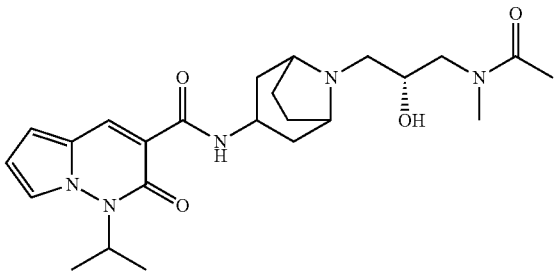 [SMILES: CC(=O)N(C)C[C@H](O)CN1C2CCC1CC(NC(=O)c1cc3cccn3n(C(C)C)c1=O)C2]<br>(R)-N-{8-[2-Hydroxy-3-[(N-methyl)acetamido]propyl]-8-azabicyclo[3.2.1]oct-3-yl} [1-isopropyl-2-oxo-1,2-dihydro pyrrolo[1,2-b]pyridazine]-3-carboxamide | Yield: 0.05 g; $^1$H-NMR (DMSO-d$_6$, 400 MHz) δ ppm: 1.57-1.58 (d, J = 6.96 Hz, 6H), 1.77 (s, 6H), 1.90-1.93 (m, 4H), 2.05-2.15 (m, 2H), 2.30-2.34 (m, 2H), 2.71-2.72 (m, 1H), 3.63-3.66 (m, 4H), 4.09-4.11 (m, 2H), 4.48-4.49 (m, 1H), 4.66-4.71 (m, 1H), 5.52-5.53 (bs, 1H), 6.64-6.65 (dd, J = 2.96, 7.08 Hz, 1H), 6.84-6.85 (d, J = 4.12 Hz, 1H), 8.01 (s, 1H), 8.47 (s, 1H), 9.99-10.01 (d, J = 7.28 Hz, 1H); Mass (m/z): 458.3 (M + H)$^+$. |
| 16 | 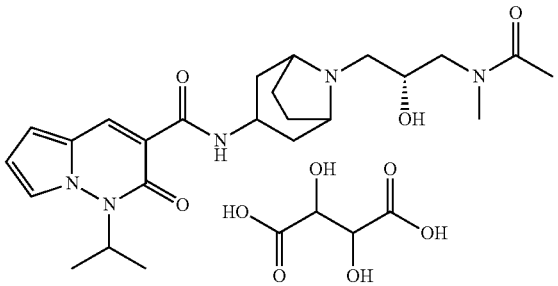 | Yield: 0.03 g; $^1$H-NMR (CD$_3$OD, 400 MHz) δ ppm: 1.66-1.68 (d, J = 6.9 Hz, 6H), 1.86 (s, 6H), 2.11-2.25 (m, 4H), 2.30-2.35 (m, 2H), 2.53-2.60 (m, 2H), 2.91-2.98 (m, 1H), 3.72-3.90 (m, 4H), 4.12-4.31 (m, 2H), 4.58-4.59 (m, 1H), 4.68-4.73 (m, 1H), 5.56-5.58 (bs, 1H), 6.68 (s, 1H), 6.84-6.85 (d, J = 4.1 Hz, 1H), 8.05 (s, 1H), 8.52 (s, 1H), 10.64-10.66 (d, J = 6.9 Hz, 1H); Mass (m/z): 458.2 (M + H)$^+$. |

| Example No. | Chemical structure and IUPAC Name | Characterization Data |
|---|---|---|
| 17 | 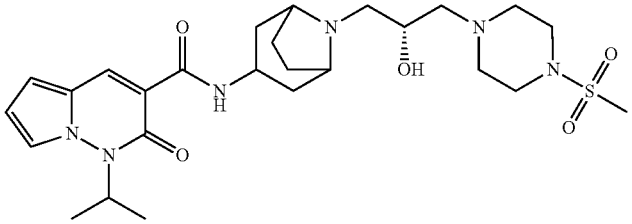 [SMILES: CC(C)n1c(=O)c(C(=O)NC2CC3CCC(C2)N3C[C@@H](O)CN2CCN(S(C)(=O)=O)CC2)cc2cccn21]<br>(R)-N-{8-[2-hydroxy-3-[(N-methyl) acetamido]propyl]-8-azabicyclo[3.2.1]oct-3-yl} [1-isopropyl-2-oxo-1,2-dihydro pyrrolo[1,2-b]pyridazine]-3-carboxamide L-(+)-tartrate | Yield: 0.12 g; $^1$H-NMR (DMSO-$d_6$, 400 MHz) δ ppm: 1.23-1.26 (m, 2H), 1.55-1.56 (d, J = 6.58 Hz, 6H), 1.89-1.96 (m, 4H), 2.15-2.31 (m, 4H), 2.34-2.48 (m, 4H), 2.87 (s, 3H), 2.92-2.96 (m, 2H), 3.01-3.10 (m, 6H), 3.52-3.68 (m, 1H), 3.91-4.01 (m, 1H), 4.06-4.18 (m, 1H), 5.43-5.56 (m, 1H), 6.66 (s, 1H), 6.68 (s, 1H), 8.02 (s, 1H), 8.49 (s, 1H), 10.10-10.11 (d, J = 6.4 Hz, 1H); Mass (m/z): 549.4 (M + H)$^+$. |
| 18 | 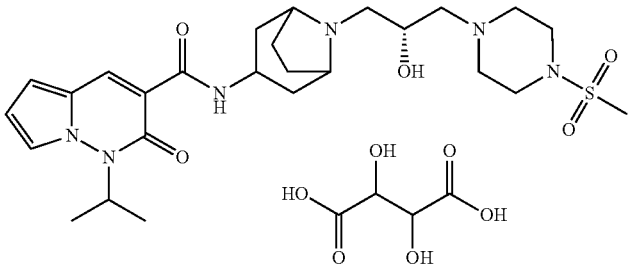 [SMILES: CC(C)n1c(=O)c(C(=O)NC2CC3CCC(C2)N3C[C@@H](O)CN2CCN(S(C)(=O)=O)CC2)cc2cccn21 ; O=C(O)C(O)C(O)C(=O)O]<br>(R)-N-{8-[2-Hydroxy-3-[(1-methanesulfonyl piperazin)-4-yl] propyl]-8-azabicyclo[3.2.1]oct-3-yl} [1-isopropyl-2-oxo-1,2-dihydro pyrrolo[1,2-b]pyridazin]-3-carboxamide L(+)tartarate | Yield: 0.13 g; $^1$H-NMR (DMSO-$d_6$, 400 MHz) δ ppm: 1.54-1.56 (d, J = 6.98 Hz, 6H), 1.78-1.82 (m, 2H), 2.08-2.13 (m, 4H), 2.36-2.43 (m, 4H), 2.52-2.53 (m, 4H), 2.67-2.69 (m, 2H), 2.86 (s, 3H), 3.71-3.82 (m, 4H), 3.95 (m, 2H), 4.07-4.12 (m, 3H), 5.51 (bs, 1H), 6.64-6.66 (dd, J = 3.72 Hz, 6.88 Hz, 1H), 6.85-6.86 (d, J = 4.2 Hz, 1H), 7.85 (s, 1H), 8.48 (s, 1H), 10.06-10.07 (d, J = 7.36 Hz, 1H); Mass (m/z): 549.8 (M + H)$^+$. |
| 19 | 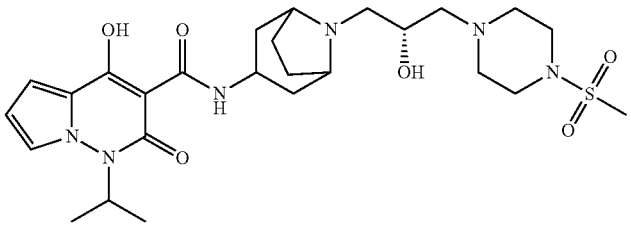 [SMILES: CC(C)n1c(=O)c(C(=O)NC2CC3CCC(C2)N3C[C@@H](O)CN2CCN(S(C)(=O)=O)CC2)c(O)c2cccn21]<br>(R)-N-{8-[2-Hydroxy-3-[(1-methanesulfonyl piperazin)-4-yl] propyl]-8-azabicyclo[3.2.1]oct-3-yl} [4-hydroxy-1-isopropyl-2-oxo-1,2-dihydro pyrrolo[1,2-b]pyridazin]-3-carboxamide | Yield: 0.25 g; $^1$H-NMR (DMSO-$d_6$, 400 MHz) δ ppm: 1.18-1.32 (m, 2H), 1.35-1.48 (m, 1H), 1.50-1.52 (d, J = 6.82 Hz, 6H), 1.60-1.66 (m, 2H), 1.81-2.08 (m, 5H), 2.18-2.41 (m, 5H), 2.69-2.78 (m, 2H), 2.86 (s, 3H), 2.98-3.12 (m, 6H), 3.64-3.73 (m, 1H), 4.09-4.10 (d, J = 4.86 Hz, 1H), 5.31-5.42 (m, 1H), 6.57 (s, 1H), 6.84-6.85 (d, J = 3.2 Hz, 1H), 7.91 (s, 1H), 10.50 (bs, 1H), 17.30 (bs, 1H); Mass (m/z): 565.3 (M + H)$^+$. |
| 20 | 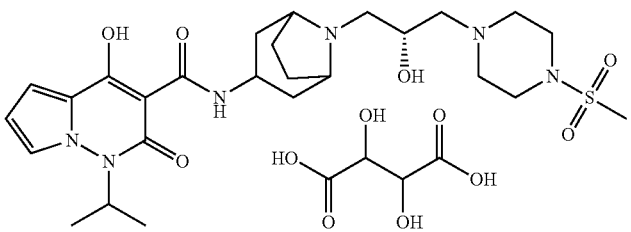 | Yield: 0.29 g; $^1$H-NMR (CD$_3$OD, 400 MHz) δ ppm: 1.61-1.62 (d, J = 7.15 Hz, 6H), 2.11-2.22 (m, 4H), 2.32-2.48 (m, 5H), 2.49-2.61 (m, 4H), 2.63-2.74 (m, 6H), 2.85 (s, 3H), 3.02-3.15 (m, 2H), 4.11 (s, 1H), 4.14-4.32 (m, 3H), 4.45 (s, 2H), 5.45-5.49 (m, 1H), 6.58-6.60 (t, J = 3.1, 7.0 Hz, 1H), 6.90-6.91 (d, J = 4.1 Hz, 1H), 7.75 (s, 1H); Mass (m/z): 565.5 (M + H)$^+$. |

| Example No. | Chemical structure and IUPAC Name | Characterization Data |
|---|---|---|
| | (R)-N-{8-[2-Hydroxy-3-[(1-methanesulfonyl piperazin)-4-yl] propyl]-8-azabicyclo[3.2.1]oct-3-yl} [4-hydroxy-1-isopropyl-2-oxo-1,2-dihydro pyrrolo[1,2-b]pyridazin]-3-carboxamide L-(+)-tartarate | |

Example 21: N-{8-[3-[(N-Methyl) methanesulfonamido]propyl]-8-azabicyclo[3.2.1]oct-3-yl}[1-isopropyl-2-oxo-1,2-dihydro pyrrolo[1,2-b]pyridazine]-3-carboxamide

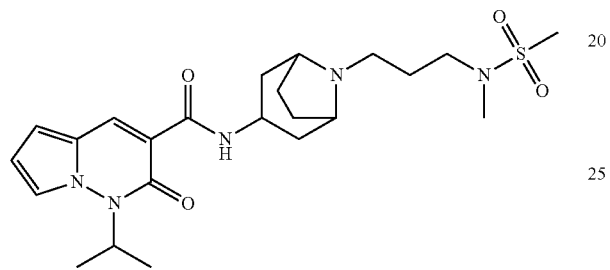

Step 1: K$_2$CO$_3$ (0.019 g, 0.13 mmol) was added in portions to a stirred solution of [N-(8-azabicyclo[3.2.1]oct-3-yl)]-1-isopropyl-2-oxo-1,2-dihydro-pyrrolo[1,2-b]pyridazine-3-carboxamide (intermediate 18, 30 mg, 0.091 mmol) and 1-bromo-3-chloropropane (0.013 mL, 0.13 mmol) in CH$_3$CN (10 mL) at RT and then refluxed for 22 h. The reaction mixture was cooled to RT, filtered and concentrated under vacuum to obtain N-[8-(3-chloro propyl)-8-azabicyclo[3.2.1]oct-3-yl][1-isopropyl-2-oxo-1,2-dihydro pyrrolo[1,2-b]pyridazine]-3-carboxamide. Yield: 0.02 g; Mass (m/z): 406.3 (M+H)$^+$.

Step 2: K$_2$CO$_3$ (0.019 g, 0.13 mmol) was added in portions to a stirred solution of N-methylmethanesulfonamide (10 mg, 0.091 mmol) and N-[8-(3-chloro propyl)-8-azabicyclo[3.2.1]oct-3-yl][1-isopropyl-2-oxo-1,2-dihydro pyrrolo[1,2-b]pyridazine]-3-carboxamide (0.044 mg, 0.11 mmol) in CH$_3$CN (10 mL) at RT and then refluxed for 22 h. The reaction mixture was cooled to RT, filtered and concentrated under vacuum to obtain a crude mass which was purified by preparative thin layer chromatography using methanol: chloroform (25:75) to obtain title compound. Yield: 15 mg; $^1$H-NMR (CD$_3$O D, 400 MHz) δ ppm: 1.66-1.68 (d, J=6.9 Hz, 6H), 2.04-2.07 (m, 2H), 2.17-2.21 (m, 2H), 2.43-2.48 (m, 6H), 2.91 (s, 6H), 3.15-3.17 (m, 2H), 4.09 (s, 2H), 4.29-4.30 (m, 1H), 4.42 (s, 2H), 5.50-5.57 (m, 1H), 6.70-6.71 (d, J=2.6 Hz, 1H), 6.85-6.86 (d, J=4.2 Hz, 1H), 7.90 (s, 1H), 8.53 (s, 1H), 10.66-10.67 (d, J=6.2 Hz, 1H); Mass (m/z): 478.4 (M+H)$^+$.

Example 22: N-{8-[3-[(N-Methyl) methanesulfonamido]propyl]-8-azabicyclo[3.2.1]oct-3-yl}[1-isopropyl-2-oxo-1,2-dihydro pyrrolo[1,2-b]pyridazine]-3-carboxamide L-(+)-tartarate

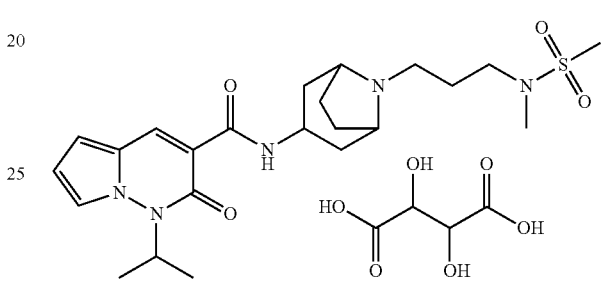

The compound of example 21 was converted to L-(+)-tartarate salt, example 22, using a similar procedure as given in the preparation of example 2. $^1$H-NMR (CD$_3$O D, 400 MHz) δ ppm: 1.66-1.68 (d, J=6.9 Hz, 6H), 2.04-2.07 (m, 2H), 2.17-2.21 (m, 2H), 2.43-2.48 (m, 4H), 2.91 (s, 6H), 3.15-3.17 (m, 3H), 4.09 (s, 2H), 4.29-4.30 (m, 1H), 4.42 (s, 2H), 5.50-5.57 (m, 2H), 6.70-6.71 (d, J=2.6 Hz, 1H), 6.85-6.86 (d, J=4.2 Hz, 1H), 7.90 (s, 1H), 8.53 (s, 1H), 10.66-10.67 (d, J=6.2 Hz, 1H); Mass (m/z): 478.4 (M+H)$^+$.

Example 23: N-{8-[3-[methanesulfonamido]propyl]-8-azabicyclo[3.2.1]oct-3-yl}[1-isopropyl-2-oxo-1,2-dihydro pyrrolo[1,2-b]pyridazine]-3-carboxamide

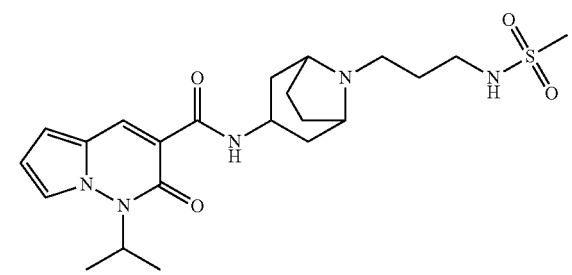 [SMILES: CC(C)n1c(=O)c(C(=O)NC2CC3CCC(C2)N3CCCNS(C)(=O)=O)cc2cccn21]

K$_2$CO$_3$ (0.019 g, 0.13 mmol) was added in portions to a stirred solution of N-(3-bromo-propyl)-methanesulfonamide (intermediate 11, 0.13 g, 0.609 mmol) and [N-(8-azabicyclo[3.2.1]oct-3-yl)]-1-isopropyl-2-oxo-1,2-dihydro-pyrrolo[1,2-b]pyridazine-3-carboxamide (intermediate 18, 0.1 g, 0.304 mmol) in CH$_3$CN (5 mL) at RT and the reaction mixture was heated at reflux temperature for 8 h. The reaction mixture was cooled to RT, poured over ice cold water, extracted with EtOAc (30 mL×3), washed with brine solution (30 mL), dried over anhydrous Na₂SO₄, filtered and concentrated under vacuum to obtain crude mass which was purified by column chromatography using methanol: DCM (1:99) to obtain the title compound. Yield: 0.1 g; ¹H-NMR (DMSO-d₆, 400 MHz) δ ppm: 1.56-1.57 (d, J=6.9 Hz, 61), 1.88-1.90 (n, 21), 2.01-2.04 (m, 2H), 2.22-2.32 (m, 4H), 2.48-2.49 (n, 21), 2.92 (s, 31), 3.01 (m, 3H), 4.01 (s, 2H), 4.14 (s, 1H), 5.52 (s, 1H), 6.66 (s, 1H), 6.87 (s, 1H), 7.13 (s, 4H), 8.03 (s, dH), 8.50 (s, 1H), 9.30 (s, 1H), 10.09 (s, 1H); Mass (m/z): 464.3 (M+H)⁺.

The following examples 24 to 36 were prepared by using the procedure as described for example 23 and example 2 with some non-critical variations using suitable intermediates.

| Example No. | Chemical structure and IUPAC Name | Characterization Data |
|---|---|---|
| 24 | 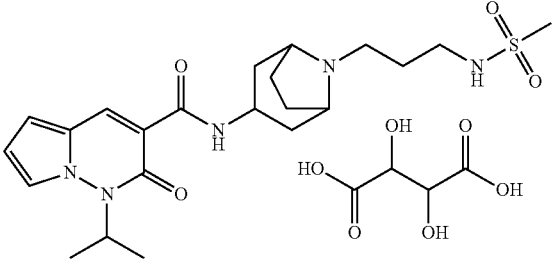<br>N-{8-[3-[methanesulfonamido]propyl]-8-azabicyclo[3.2.1]oct-3-yl} [1-isopropyl-2-oxo-1,2-dihydro pyrrolo[1,2-b]pyridazine]-3-carboxamide L-(+)-tartarate | Yield: 0.1 g; ¹H-NMR (CD₃OD, 400 MHz) δ ppm: 1.66-1.68 (d, J = 6.9 Hz, 6H), 2.08-2.09 (m, 2H), 2.15-2.19 (m, 2H), 2.20-2.32 (m, 4H), 2.48-2.52 (m, 2H), 2.95 (s, 3H), 3.10-3.24 (m, 3H), 4.12 (s, 2H), 4.26 (s, 1H), 5.56 (s, 1H), 6.66 (s, 1H), 6.88 (s, 1H), 7.14 (s, 1H), 8.04 (s, 1H), 8.52 (s, 1H), 9.30 (s, 1H), 10.64 (s, 1H); Mass (m/z): 464.4 (M + H)⁺. |
| 25 | 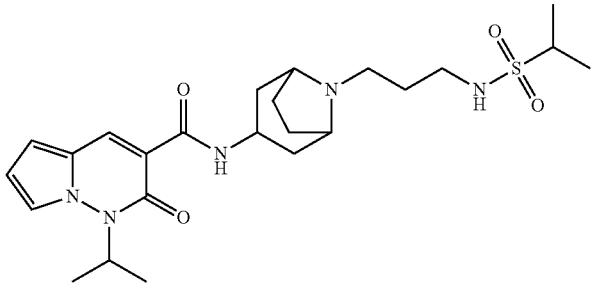 [SMILES: CC(C)n1c(=O)c(C(=O)NC2CC3CCC(C2)N3CCCNS(=O)(=O)C(C)C)cc2cccn21]<br>N-{8-[3-Isopropylsulfonylaminopropyl]-8-azabicyclo[3.2.1]oct-3-yl} [1-isopropyl-2-oxo-1,2-dihydro pyrrolo[1,2-b]pyridazin]-3-carboxamide | Yield: 0.25 g; ¹H-NMR (DMSO-d₆, 400 MHz) δ ppm: 1.21-1.23 (d, J = 6.8 Hz, 6H), 1.53-1.56 (m, 8H), 1.86-1.98 (m, 5H), 2.20-2.32 (m, 4H), 2.98-3.02 (m, 3H), 3.16-3.29 (m, 2H), 3.98-4.01 (m, 2H), 5.50-5.52 (m, 1H), 6.62 (s, 1H), 6.87 (s, 1H), 7.15 (s, 1H), 8.03 (s, 1H), 8.49 (s, 1H), 10.10 (s, 1H); Mass (m/z): 492.2 (M + H)⁺. |
| 26 | 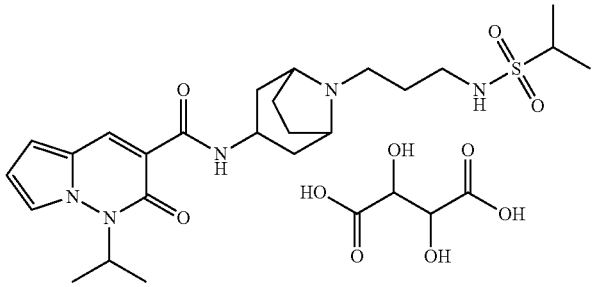<br>N-{8-[3-Isopropylsulfonylaminopropyl]-8-azabicyclo[3.2.1]oct-3-yl} [1-isopropyl-2-oxo-1,2-dihydro pyrrolo[1,2-b]pyridazin]-3-carboxamide L-(+)-tartrate | Yield: 0.26 g; ¹H-NMR (DMSO-d₆, 400 MHz) δ ppm: 1.21-1.23 (d, J = 6.8 Hz, 6H), 1.56-1.57 (m, 8H), 1.87-2.00 (m, 5H), 2.22-2.36 (m, 4H), 3.01-3.03 (m, 3H), 3.20-3.33 (m, 2H), 4.00-4.12 (m, 2H), 5.53-5.54 (m, 1H), 6.66 (s, 1H), 6.87 (s, 1H), 7.15 (s, 1H), 8.03 (s, 1H), 8.49 (s, 1H), 10.10 (s, 1H); Mass (m/z): 492.2 (M + H)⁺. |

| Example No. | Chemical structure and IUPAC Name | Characterization Data |
|---|---|---|
| 27 | 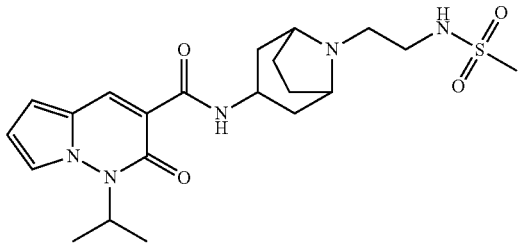 [SMILES: CC(C)n1c(=O)c(C(=O)NC2CC3CCC(C2)N3CCNS(C)(=O)=O)cc2cccn21]<br>N-{8-[2-Methanesulfonylaminoethyl]-8-azabicyclo[3.2.1]oct-3-yl} [1-isopropyl-2-oxo-1,2-dihydro pyrrolo[1,2-]pyridaazin]-3-carboxamide | Yield: 0.35 g; $^1$H-NMR (CDCl$_3$, 400 MHz) δ ppm: 1.63-1.65 (d, J = 7.0 Hz, 6H), 1.83-1.87 (m, 2H), 2.08-2.17 (m, 4H), 2.28-2.35 (m, 2H), 2.70 (m, 2H), 2.98 (s, 3H), 3.24-3.28 (m, 2H), 3.35-3.37 (m, 2H), 4.25-4.30 (m, 1H), 4.73 (s, 1H), 5.70 (s, 1H), 6.59 (s, 1H), 6.69-6.70 (d, J = 4.0 Hz, 1H), 7.45 (s, 1H), 8.56 (s, 1H), 10.09-10.11 (d, J = 6.8 Hz, 1H); Mass (m/z): 450.2 (M + H)$^+$. |
| 28 | 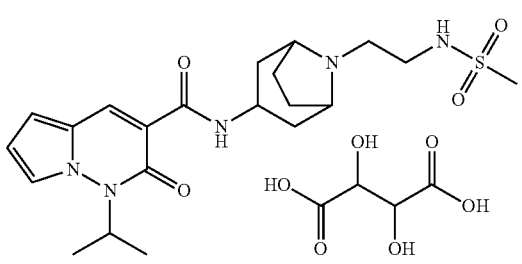<br>N-{8-[2-Methanesulfonylaminoethyl]-8-azabicyclo[3.2.1]oct-3-yl} [1-isopropyl-2-oxo-1,2-dihydro pyrrolo[1,2-b]pyridazin]-3-carboxamide L-(+)-tartrate | Yield: 0.18 g; $^1$H-NMR (CD$_3$OD, 400 MHz) δ ppm: 1.66-1.68 (d, J = 7.0 Hz, 6H), 2.13-2.17 (m, 2H), 2.38-2.48 (m, 4H), 2.55-2.59 (m, 2H), 3.04 (s, 3H), 3.24-3.28 (m, 2H), 3.50-3.53 (m, 2H), 4.13-4.14 (m, 2H), 4.45 (s, 2H), 5.51-5.59 (m, 1H), 6.69-6.71 (dd, J = 2.9, 4.2 Hz, 1H), 6.85-6.86 (d, J = 4.1 Hz, 1H), 7.89 (s, 1H), 8.52 (s, 1H), 10.63-10.65 (d, J = 6.8 Hz, 1H); Mass (m/z): 450.2 (M + H)$^+$. |
| 29 | 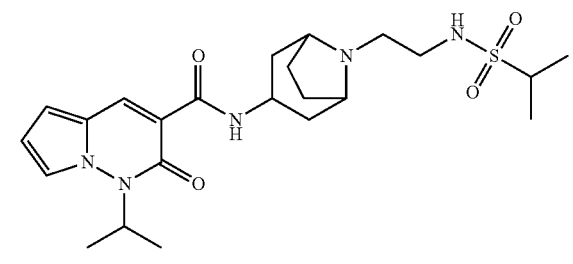 [SMILES: CC(C)n1c(=O)c(C(=O)NC2CC3CCC(C2)N3CCNS(=O)(=O)C(C)C)cc2cccn21]<br>N-{8-[2-Isopropylsulfonylaminoethyl]-8-azabicyclo[3.2.1]oct-3-yl} [1-isopropyl-2-oxo-1,2-dihydro pyrrolo[1,2-b]pyridazin]-3-carboxamide | Yield: 0.21 g; $^1$H-NMR (CDCl$_3$, 400 MHz) δ ppm: 1.38-1.40 (d, J = 6.7 Hz, 6H), 1.63-1.65 (d, J = 7.1 Hz, 6H), 1.79-1.86 (m, 3H), 2.10-2.13 (m, 4H), 2.32-2.33 (m, 2H), 2.67-2.69 (m, 2H), 3.09-3.11 (m, 2H), 3.24-3.27 (m, 2H), 3.38-3.39 (m, 2H), 4.26-4.31 (m, 1H), 6.58-6.59 (dd, J = 2.7, 4.2 Hz, 1H), 6.69-6.70 (d, J = 4.0 Hz, 1H), 7.45 (s, 1H), 8.56 (s, 1H), 10.10-10.12 (d, J = 7.0 Hz, 1H); Mass (m/z): 478.3 (M + H)$^+$. |
| 30 | 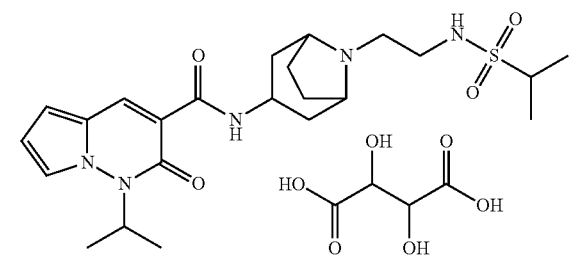<br>N-{8-[2-Isopropylsulfonylaminoethyl]-8-azabicyclo[3.2.1]oct-3-yl} [1-isopropyl-2-oxo-1,2-dihydro pyrrolo[1,2-b]pyridazin]-3-carboxamide L-(+)-tartrate | Yield: 0.2 g; $^1$H-NMR (CDCl$_3$OD, 400 MHz) δ ppm: 1.38-1.40 (d, J = 6.7 Hz, 6H), 1.66-1.68 (d, J = 7.1 Hz, 6H), 2.13-2.17 (m, 3H), 2.38-2.48 (m, 4H), 2.50-2.55 (m, 2H), 2.70-2.79 (m, 2H), 3.19-3.21 (m, 2H), 3.34-3.42 (m, 2H), 4.42-4.45 (m, 2H), 5.50-5.59 (m, 1H), 6.59 (s, 1H), 6.69-6.70 (s, 1H), 7.86 (s, 1H), 8.56 (s, 1H), 10.10-10.12 (d, J = 7.0 Hz, 1H); Mass (m/z): 478.3 (M + H)$^+$. |

| Example No. | Chemical structure and IUPAC Name | Characterization Data |
|---|---|---|
| 31 | 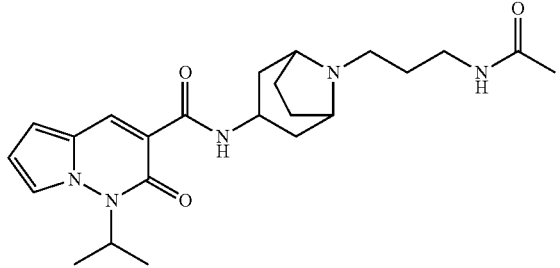 [SMILES: CC(=O)NCCCN1C2CCC1CC(NC(=O)c1cc3cccn3n(C(C)C)c1=O)C2]<br>N-{8-[3-Acetamidopropyl]-8-azabicyclo[3.2.1]oct-3-yl} [1-isopropyl-2-oxo-1,2-dihydro pyrrolo[1,2-b]pyridazin]-3-carboxamide | Yield: 0.12 g; Mass (m/z): 428.2 $(M + H)^+$. |
| 32 | 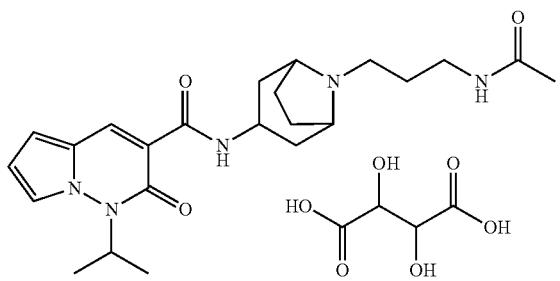 [SMILES: CC(=O)NCCCN1C2CCC1CC(NC(=O)c1cc3cccn3n(C(C)C)c1=O)C2 ; O=C(O)C(O)C(O)C(=O)O]<br>N-{8-[3-Acetamidopropyl]-8-azabicyclo[3.2.1]oct-3-yl} [1-isopropyl-2-oxo-1,2-dihydro pyrrolo[1,2-pyridazin]-3-carboxamide L-(+)-tartrate | Yield: 0.13 g; $^1$H-NMR (CD$_3$OD, 400 MHz) δ ppm: 1.64-1.66 (d, J = 7.2 Hz, 6H), 2.08-2.09 (m, 2H), 2.11-2.18 (m, 2H), 2.20-2.28 (m, 4H), 2.30-2.56 (m, 6H), 3.08-3.12 (m, 3H), 4.05 (bs, 2H), 4.27-4.28 (m, 1H), 4.49 (s, 2H), 6.68 (s, 1H), 6.83-6.84 (d, J = 4.0 Hz, 1H), 7.87 (s, 1H), 8.50 (s, 1H), 10.66 (s, 1H); Mass (m/z): 428.2 $(M + H)^+$. |
| 33 | 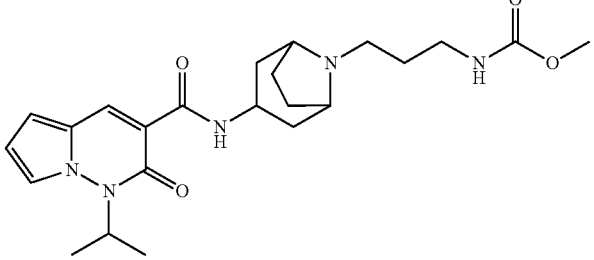<br>N-{8-[3-Carbomethoxyaminopropyl]-8-azabicyclo[3.2.1]oct-3-yl} [1-isopropyl-2-oxo-1,2-dihydro pyrrolo[1,2-b]pyridazin]-3-carboxamide | Yield: 0.21 g; $^1$H-NMR (DMSO-d$_6$, 400 MHz) δ ppm: 1.56-1.57 (d, J = 6.8 Hz, 6H), 1.75-1.82 (m, 2H), 1.98-2.02 (m, 3H), 2.20-2.25 (m, 4H), 2.49-2.50 (m, 3H), 2.89-2.92 (m, 2H), 3.04-3.06 (m, 2H), 3.53 (s, 3H), 3.98-4.12 (m, 2H), 5.53 (s, 1H), 6.66-6.67 (dd, J = 3.2, 6.8 Hz, 1H), 6.87-6.88 (d, J = 4.0 Hz, 1H), 8.03 (s, 1H), 8.50 (s, 1H), 10.09 (s, 1H); Mass (m/z): 444.1 $(M + H)^+$. |
| 34 | 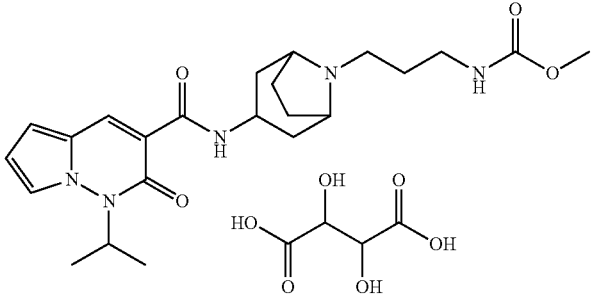 | Yield: 0.24 g; $^1$H-NMR (CD$_3$OD, 400 MHz) δ ppm: 1.64-1.66 (d, J = 7.2 Hz, 6H), 1.93 (bs, 2H), 2.14-2.20 (m, 2H), 2.40-2.50 (m, 6H), 2.85 (s, 1H), 2.98 (s, 1H), 3.08-3.12 (m, 2H), 3.21-3.24 (m, 2H), 3.65 (s, 1H), 4.05 (bs, 2H), 4.27-4.28 (m, 1H), 4.49 (s, 2H), 6.68 (s, 1H), 6.83-6.84 (d, J = 4.0 Hz, 1H), 7.87 (s, 1H), 8.50 (s, 1H), 10.63 (s, 1H); Mass (m/z): 444.2 $(M + H)^+$. |

| Example No. | Chemical structure and IUPAC Name | Characterization Data |
|---|---|---|
| 35 | 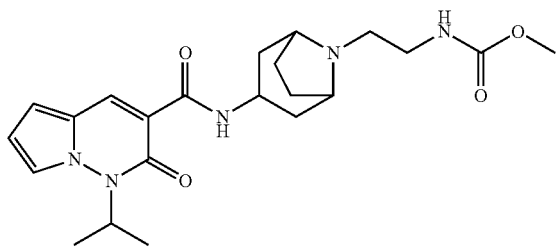 [SMILES: COC(=O)NCCN1C2CCC1CC(NC(=O)c1cc3cccn3n(C(C)C)c1=O)C2]<br>N-{8-[3-Carbomethoxyaminopropyl]-8-azabicyclo[3.2.1]oct-3-yl} [1-isopropyl-2-oxo-1,2-dihydro pyrrolo[1,2-b]pyridazin]-3-carboxamide L-(+)-tartrate | Yield: 0.10 g; $^1$H-NMR (CDCl$_3$, 400 MHz) δ ppm: 1.63-1.65 (d, J = 7.1 Hz, 6H), 1.72-1.86 (m, 3H), 2.02-2.26 (m, 5H), 2.61-2.72 (m, 2H), 3.30-3.43 (m, 4H), 3.80 (s, 3H), 4.31 (s, 1H), 5.30 (s, 1H), 5.71 (s, 1H), 6.58-6.60 (dd, J = 2.9, 4.2 Hz, 1H), 6.69-6.70 (d, J = 4.1 Hz, 1H), 7.46 (s, 1H), 8.56 (s, 1H), 10.12 (s, 1H); Mass (m/z): 430.4 (M + H)$^+$. |
| | N-{8-[2-Carbomethoxyaminomethyl]-8-azabicyclo[3.2.1]oct-3-yl} [1-isopropyl-2-oxo-1,2-dihydro pyrrolo[1,2-b]pyridazin]-3-carboxamide | |
| 36 | 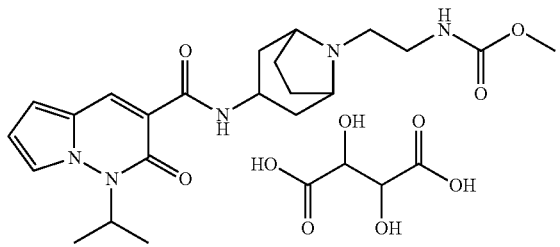<br>N-{8-[2-Carbomethoxyaminoethyl]-8-azabicyclo[3.2.1]oct-3-yl} [1-isopropyl-2-oxo-1,2-dihydro pyrrolo[1,2-b]pyridazin]-3-carboxamide L-(+)-tartrate | Yield: g; $^1$H-NMR (CD$_3$OD, 400 MHz) δ ppm: 1.66-1.68 (d, J = 7.0 Hz, 6H), 2.10-2.18 (m, 3H), 2.46-2.49 (m, 5H), 2.56-2.61 (m, 2H), 3.32-3.45 (m, 4H), 3.88 (s, 3H), 4.38 (s, 1H), 5.56 (s, 1H), 5.88 (s, 1H), 6.68 (s, 1H), 6.85-6.86 (d, J = 4.1 Hz, 1H), 7.89 (s, 1H), 8.62 (s, 1H), 10.06 (s, 1H); Mass (m/z): 430.4 (M + H)$^+$. |

Example 37: N-{8-[2-(4-Acetyl piperazin-1-yl) ethyl]-8-azabicyclo[3.2.1]oct-3-yl}[1-isopropyl-2-oxo-1,2-dihydro pyrrolo[1,2-b]pyridazine]-3-carboxamide

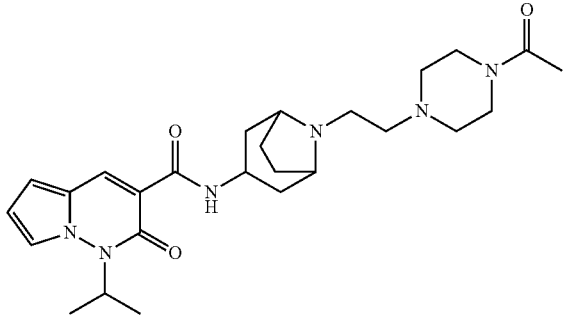 [SMILES: CC(=O)N1CCN(CCN2C3CCC2CC(NC(=O)c2cc4cccn4n(C(C)C)c2=O)C3)CC1]

DIPEA (0.47 mL, 2.72 mmol), HATU (0.28 g, 0.75 mmol) were added to a stirred solution of 1-isopropyl-2-oxo-1,2-dihydro pyrrolo[1,2-b]pyridazine-3-carboxylic acid (intermediate 1, 0.15 g, 0.68 mmol) in DMF (2 mL) at RT, stirred for 2 h followed by addition of 1-{4-[2-(3-amino-8-azabicyclo[3.2.1]oct-8-yl) ethyl]piperazin-1-yl} ethanone (intermediate 10, 0.23 g, 0.81 mmol) and stirred for 20 h. The reaction mixture was poured on to water (50 mL) under stirring during which solids precipitated. These solids were filtered, dissolved in DCM (50 mL), washed with brine solution (25 mL), dried over anhydrous Na$_2$SO$_4$, filtered and concentrated under vacuum to obtain the title compound. Yield: 0.06 g; $^1$H-NMR (DMSO-d$_6$, 400 MHz) δ ppm: 1.56-1.57 (d, J=6.9 Hz, 6H), 1.88-1.90 (m, 2H), 1.97 (s, 3H), 2.06-2.08 (m, 2H), 2.33 (m, 2H), 2.40-2.41 (m, 7H), 3.18 (bs, 3H), 3.37-3.39 (m, 6H), 4.06-4.10 (m, 1H), 5.53 (bs, 1H), 6.64-6.66 (dd, J=2.9, 4.0 Hz, 1H), 6.84-6.85 (d, J=4.1 Hz, 1H), 8.0 (s, 1H), 8.48 (s, 1H), 9.99-10.01 (d, J=8.0 Hz, 1H); Mass (m/z): 483.4 (M+H)$^+$.

Example 38: N-{8-[2-(4-Acetyl piperazin-1-yl) ethyl]-8-azabicyclo[3.2.1]oct-3-yl}[1-isopropyl-2-oxo-1,2-dihydro pyrrolo[1,2-b]pyridazine]-3-carboxamide L-(+)-tartrate

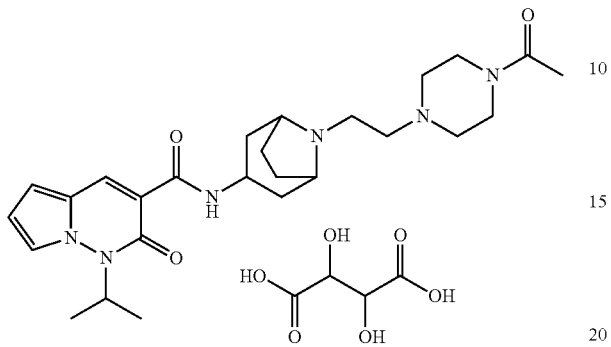

The compound of example 37 was converted to L-(+)-tartarate salt, example 38, using a similar procedure as given in the preparation of example 2. Yield: 0.05 g; $^1$H-NMR (CD$_3$O D, 400 MHz) δ ppm: 1.61-1.64 (d, J=6.9 Hz, 6H), 2.04-2.11 (m, 2H), 2.20 (s, 3H), 2.26-2.32 (m, 2H), 2.38 (m, 2H), 2.40-2.45 (m, 7H), 3.28 (bs, 3H), 3.38-3.40 (m, 6H), 4.21-4.38 (m, 1H), 5.58 (bs, 1H), 6.66 (s, 1H), 6.84-6.85 (d, J=4.1 Hz, 1H), 7.98 (s, 1H), 8.48 (s, 1H), 10.62 (s, 1H); Mass (m/z): 483.4 (M+H)$^+$.

Example 39: N-{8-[2-(4-Acetyl piperazin-1-yl) ethyl]-8-azabicyclo[3.2.1]oct-3-yl}[4-hydroxy-1-isopropyl-2-oxo-1,2-dihydropyrrolo[1,2-b] pyridazine]-3-carboxamide

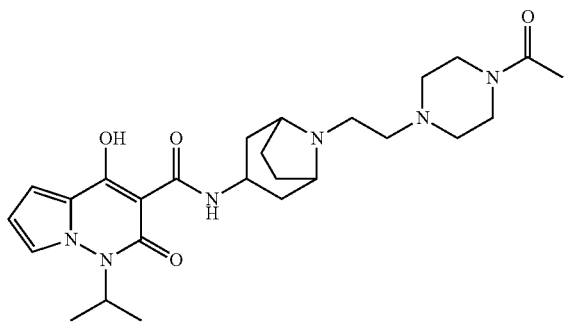 [SMILES: CC(=O)N1CCN(CCN2C3CCC2CC(NC(=O)c2c(O)c4cccn4n(C(C)C)c2=O)C3)CC1]

K$_2$CO$_3$ (0.05 g, 0.36 mmol) was added to a stirred solution of ethyl 4-hydroxy-1-isopropyl-2-oxo-1,2-dihydro pyrrolo[1,2-b]pyridazine-3-carboxylate (intermediate 2, 0.1 g, 0.36 mmol) and 1-{4-[2-(3-amino-8-azabicyclo[3.2.1] oct-8-yl) ethyl]piperazin-1-yl} ethanone (intermediate 10, 0.13 g, 0.46 mmol) in toluene (10 mL) at RT and the reaction mixture was heated at reflux temperature for 20 h. The reaction mixture was cooled to RT, poured over ice cold water, extracted with EtOAc (30 mL×3), washed with brine solution (30 mL), dried over anhydrous Na$_2$SO$_4$, filtered and concentrated under vacuum to obtain crude mass which was purified by column chromatography using methanol: DCM (5:95) to obtain the title compound. Yield: 0.06 g; Mass (m/z): 499.5 (M+H)$^+$.

Example 40: N-{8-[2-(4-Acetyl piperazin-1-yl) ethyl]-8-azabicyclo[3.2.1]oct-3-yl}[4-hydroxy-1-isopropyl-2-oxo-1,2-dihydropyrrolo[1,2-b] pyridazine]-3-carboxamide L-(+)-tartrate The compound of example 39 was converted to L-(+)-tartarate salt, example 40, using a similar procedure as given in the preparation of example 2. Yield: 0.05 g; $^1$H-NMR (CD$_3$O D, 400 MHz) δ ppm: 1.63-1.66 (d, J=6.9 Hz, 6H), 2.03-2.11 (m, 2H), 2.20 (s, 3H), 2.28-2.32 (m, 2H), 2.38 (m, 2H), 2.42-2.46 (m, 7H), 3.28 (bs, 3H), 3.38-3.40 (m, 6H), 4.28-4.38 (m, 1H), 5.56 (bs, 2H), 6.66 (s, 1H), 6.84-6.85 (d, J=4.1 Hz, 1H), 7.89 (s, 1H), 10.80 (bs, 1H); Mass (m/z): 499.6 (M+H)$^+$.

Example 41: Determination of EC$_{50}$ Values for 5-HT$_4$ Receptor

A stable CHO cell line expressing recombinant human 5-HT$_4$ receptor and pCRE-Luc reporter system was used for cell-based assay. The assay offers a non-radioactive based approach to determine binding of a compound to GPCRs. In this specific assay, the level of intracellular cyclic AMP, which is modulated by activation, or inhibition of the receptor is measured. The recombinant cells harbor luciferase reporter gene under the control of cAMP response element.

The above cells were grown in 96 well clear bottom white plates in Ham's F12 medium containing 10% fetal bovine serum. Prior to the addition of compounds or standard agonist, cells were serum starved overnight. Increasing concentrations of test compounds were added to the cells in OptiMEM medium. The incubation was continued in CO$_2$ incubator at 37° C. with 5% CO$_2$ conditions for 4 h. Medium was removed and cells were washed with phosphate buffered saline. The cells were lysed and luciferase activity was measured in a Luminometer. Concentration-response data was generated using the luciferase assay, following incubation of cells with receptor ligands, were analyzed by subtracting basal levels (i.e. with medium alone), then normalizing values as a percentage of controls (endogenous agonist serotonin (10 PM)). This data were analyzed by nonlinear regression with variable slope, using the computer package GraphPad Prism 4. EC$_{50}$ values of the compounds were defined as the concentration required in stimulating the luciferase activity by 50%.

Using this protocol, compounds described herein were found to exhibit binding affinity towards 5-HT$_4$ receptor.

| Example No | EC$_{50}$ (nM) |
|---|---|
| 1 | 2 |
| 2 | 4.1 |
| 3 | 9 |
| 4 | 10 |
| 5 | 3.1 |
| 6 | 3.3 |
| 7 | 10.1 |
| 8 | 6.1 |
| 14 | 6.3 |
| 15 | 8 |
| 18 | 2.4 |
| 20 | 14 |
| 22 | 58 |
| 24 | 11 |
| 25 | 13 |
| 28 | 12 |
| 29 | 16 |

-continued

| Example No | EC$_{50}$ (nM) |
|---|---|
| 31 | 35.1 |
| 33 | 12 |
| 34 | 18 |
| 35 | 12 |
| 38 | 15.4 |

Example 42: Rat Pharmacokinetic Study

Male Wistar rats (250±50 g) were used as experimental animals. Animals were housed individually in polypropylene cages. Two days prior to study, rats were anesthetized with isoflurane for surgical placement of jugular vein catheter. Rats were randomly divided for oral (3 mg/kg and 10 mL/kg as dose volume) and intravenous (1 mg/kg and 2 mL/kg as dose volume) dosing (n=3/group) and fasted overnight before oral dosing (p.o.). However, rats allocated to intravenous dosing food and water was provided ad libitum.

Intravenous formulation was prepared by using water for injection as vehicle. For Oral, formulation was prepared by using reagent grade water as vehicle. The dose formulations were prepared freshly on the day of dosing.

After dosing of animal, each time point a 200 μL of blood sample was collected through jugular vein and replenished with an equivalent volume of normal saline. The collected blood sample was transferred into a labeled eppendorf tube containing 10 μL of sodium heparin (1000 IU/mL) as an anticoagulant. Typically blood samples were collected at following time points: 0.08, 0.25, 0.5, 1, 2, 4, 6, 8, and 24 h post dose. Blood was centrifuged at 4000 rpm for 10 min. Plasma was separated and stored frozen at −80° C. until analysis. The concentrations of the test compounds were quantified in plasma by qualified LC-MS/MS method using a suitable extraction technique. The test compounds were quantified in the calibration range around 1-2000 ng/mL in plasma. Study samples were analyzed using calibration samples in the batch and quality control samples spread across the batch.

Pharmacokinetic parameters $C_{max}$, $AUC_t$, $t_{1/2}$ and bioavailability were calculated by non-compartmental model using standard non-compartmental model by using Phoenix WinNonlin 6.4 version Software.

| Example Number | Route of administration | $C_{max}$ (ng/mL) | $AUC_t$ (ng·h/mL) | $t_{1/2}$ (h) | Bioavailability (%) |
|---|---|---|---|---|---|
| 2 | oral (gavage) | 51 ± 19 | 160 ± 35 | — | 83 ± 18% |
|  | intravenous (bolus) | — | 65 ± 3 | 1.5 ± 0.5 |  |
| 4 | oral (gavage) | 11 ± 6.6 | 44 ± 22 | — | 12 ± 5.9% |
|  | intravenous (bolus) | — | 124 ± 7.9 | 1.7 ± 0.3 |  |
| 28 | oral (gavage) | 83 ± 51 | 189 ± 26 | — | 43 ± 6% |
|  | intravenous (bolus) | — | 146 ± 39 | 1.3 ± 0.2 |  |
| 34 | oral (gavage) | 174 ± 49 | 274 ± 74 | — | 77 ± 21% |
|  | intravenous (bolus) | — | 119 ± 16 | 1.3 ± 0.3 |  |

Example 43: Rat Brain Penetration Study

Male Wistar rats (225±25 g) were used as experimental animals. Three animals were housed in each cage. Animals were given water and food ad libitum throughout the experiment and maintained on a 12 h light/dark cycle.

Brain penetration was determined in discrete manner in rats. One day prior to dosing day, male Wistar rats were acclimatized. After acclimatization, the rats were grouped according to their weight. In each group, 3 animals were kept in individual cages and allowed free access to food and water. At each time point (0.5, 1, and 2 h) n=3 animals were used.

The compounds of formula (I) were suitably preformulated and administered orally at (free base equivalent) 3 mg/kg. Blood samples were collected via, cardiac puncture by using isoflurane anesthesia. The animals were sacrificed to collect brain tissue. Plasma was separated and brain samples were homogenized and stored frozen at −20° C. until analysis.

The concentrations of the compounds of formula (I) were quantified in plasma and brain homogenate by qualified LC-MS/MS method using a suitable extraction technique. The compounds of formula (I) were quantified in the calibration range of 1-2000 ng/mL in plasma and brain homogenate. Study samples were analyzed using calibration samples in the batch and quality control samples spread across the batch. Extent of brain-plasma ratio was calculated ($C_b/C_p$). Brain concentrations were found below LLOQ and a value of zero was considered for calculation purposes.

| Example Number | Dose (mg/kg) | Vehicle | Route of administration | Single dose Brain Penetration ($C_b/C_p$) |
|---|---|---|---|---|
| 2 | 3 | Reagent grade Water | oral (gavage) | 0 |
|  | 1 | Water for injection | intravenous (bolus) |  |

-continued

| Example Number | Dose (mg/kg) | Vehicle | Route of administration | Single dose Brain Penetration ($C_b/C_p$) |
|---|---|---|---|---|
| 4 | 3 | Reagent grade Water | oral (gavage) | 0 |
|  | 1 | Water for injection | intravenous (bolus) |  |
| 28 | 3 | Reagent grade Water | oral (gavage) | 0 |
|  | 1 | Water for injection | intravenous (bolus) |  |
| 34 | 3 | Reagent grade Water | oral (gavage) | 0 |
|  | 1 | Water for injection | intravenous (bolus) |  |

Example 44: Effect on Gastric Emptying in Beagle Dogs

Six beagle dogs were used for the study in a crossover manner such that all 6 dogs received all the treatments. Each dog was placed in an individual cage after overnight fasting and water removed. To provide a model of gastroparesis, clonidine ($\alpha_2$ adrenergic agonist) at a dose of 10 µg/kg was injected subcutaneously 30 min before test meal administration.

Dogs were orally administered test compound of example 2 at 1, 3 and 10 mg/kg or vehicle or cisapride at 10 mg/kg immediately before the administration of clonidine. The test meal (10 mL/kg), made up of commercially available semi-solid food with 10 mg/kg of acetaminophen (APAP), was provided 30 min after clonidine injection. Blood samples were collected from cephalic vein at 0, 0.25, 0.5, 0.75, 1.0, 1.25, 1.5 & 2.0 h after test meal administration and then plasma was separated by centrifugation. Plasma concentrations of APAP were determined by in-house methods using LC-MS/MS.

Results: Subcutaneous administration of clonidine (10 µg/kg) decreases postprandial muscle contractions and significantly delayed gastric emptying of liquids and solids. In clonidine-treated dogs, cisapride (10 mg/kg) restored speed of gastric emptying. The test compound of example 2 at 3 and 10 mg/kg increased gastric motor activity, and enhanced the gastric emptying in dose dependent manner confirming its pro-kinetic potential (FIG. 1).

Example 45: Effect on Colonic Transit in Swiss Mice

Male Swiss mice of body weight~20-30 g were fasted for 16 h with free access to water prior to the experiment. Mice were administrated compound of example 2 or vehicle, 30 min after administration of 0.5 ml of carmine dye solution. Mice were sacrificed 3 h after dye administration and the distance traveled by the dye from proximal colon was measured. Colonic transit was expressed as % colonic transit=100×(length of colon in which carmine moved/total length of colon).

Figure 2:
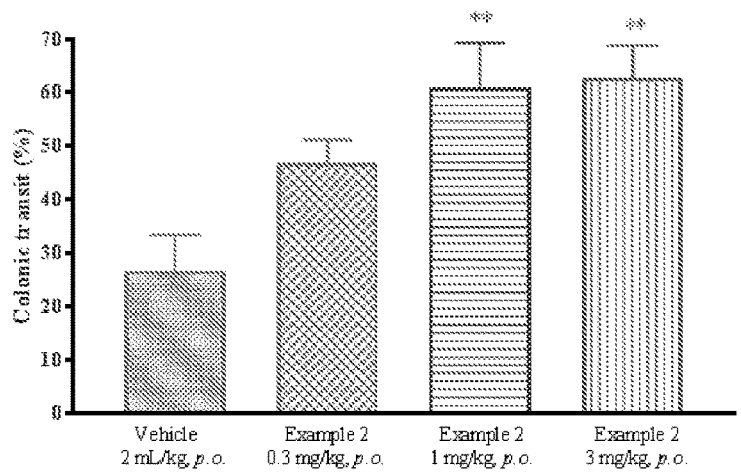
FIG. 2 depicts the colonic transit effect of Example 2 in Swiss mice.

Results: The test compound of example 2 at doses of 1 and 3 mg/kg, p.o. increased the colonic transit (FIG. 2).

Example 46: hERG Patch-Clamp Assay

The HEK293-hERG cells for patch-clamp assay were cultured in DMEM: Ham's F12 (1:1 ratio) with 10% fetal bovine serum containing 0.5 mg/ml of selective antibiotic, G-418 sulfate (Calbiochem) and 0.1% penicillin and streptomycin (Thermofisher, MA, USA) in T-75 flask. Cells were harvested at 70-80% confluency by washing with Hanks' Balanced Salt Solution lacking $Mg^{2+}$ and $Ca^{2+}$ ions and subsequent addition of accumax (2.5 mL) (Sigma Aldrich, MO, USA) and incubated the flask at 5% $CO_2$ and 37° C. until cells start sliding of the surface. After cells have completely detached from the surface about 10 mL of complete media without selective antibiotic was added and pipetted to detach the cell clumps. Additional 7.5 mL of complete media was added to collect the residual cells in the flask and cell suspension was incubated at 5% $CO_2$ and 37° C. for 30 min. Centrifuged at 200×g for 2 min, supernatant was discarded and cell pellet was re-suspended in external solution which will be used for patch-clamp assay. hERG Patch-clamp assay was performed using the external solution of 140 mM NaCl, 4 mM KCl, 1 mM $MgCl_2$, 2 mM $CaCl_2$, 5 mM D-Glucose monohydrate, 10 mM HEPES/NaOH, pH 7.4, Osmolarity: 298 mOsmol and internal solution of 50 mM KCl, 10 mM NaCl, 60 mM KF, 20 mM ethylene glycol tetraacetic acid, 10 mM HEPES/KOH, pH 7.2, Osmolarity 285 mOsmol. Whole cell patch-clamp recordings were performed by using the I-V protocol of holding HEK293-hERG cells at −80 mV and stepping to +40 mV for 500 ms and followed by 500 ms step to −40 mV before stepping back to holding potential. The peak current is measured at −40 mV tail currents using Patchliner instrument. The I-V pulse protocol was pulsed every 10 s and online analysis were recorded by substituting the leak current from the peak current and $IC_{50}$ values were calculated from IGOR PRO software (WaveMetrics, Inc. Portland, OR, USA).

Results: Example 2 was evaluated in the hERG patch-clamp assay and half maximal inhibitory concentration of hERG tail currents was $IC_{50}$>10 µM.

Example 47: Intestinal Myoelectrical Activity in Male Wistar Rats

Method: The telemetry transmitter (F40-EET; DSI, MA, USA) was implanted subcutaneously in the rat and the spring electrodes were implanted into the walls of intestine (jejunum) under isoflurane anesthesia. After two weeks of surgical recovery, animals were fasted for 14 h and transferred to recording cages. The transmitter was switched on using magnetic switch and baseline intestinal EMG activity was recorded for 3 h. Rats were treated with vehicle, test compound of example 2 (10 or 30 mg/kg, p.o.) or positive control, prucalopride (10 mg/kg, p.o.) was administered and EMG signals were recorded for additional 3 h using Ponemah software (DSI, MA, USA). Animals were given access to only water during study. The recorded EMG signal was filtered using 20-50 Hz band filter and spiking activity was measured in bouts of 30 min using NeuroScore software (DSI, MA, USA).

Figure 3:
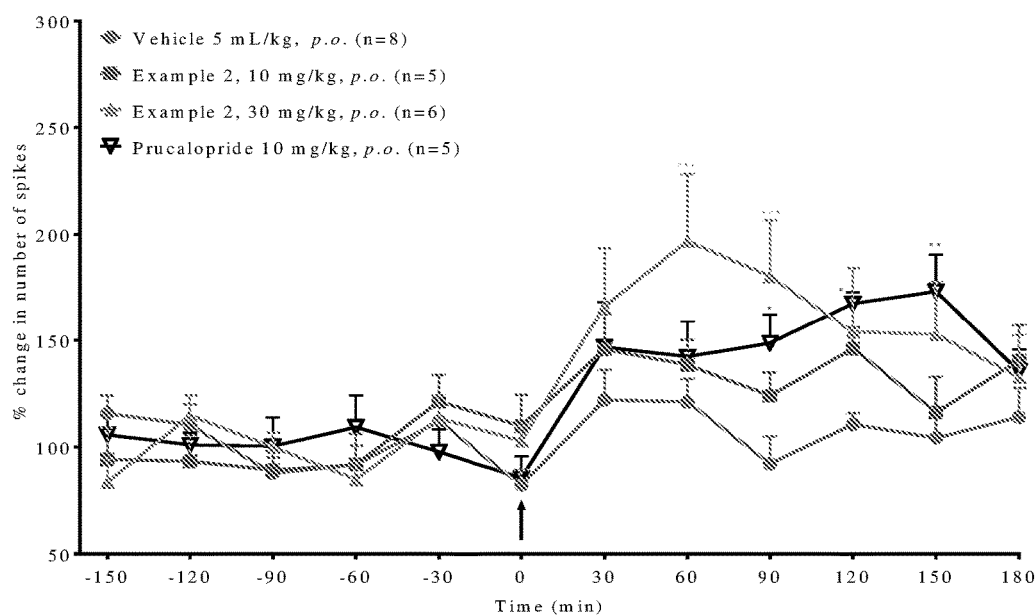
FIG. 3 depicts the intestinal myoelectrical activity of Example 2 in male Wistar rats.

Results: Example 2 produced dose-dependent increase in myoelectric activity with 97±31% increases at 30 mg/kg, p.o. The increased spiking activity is in line with Prucalopride (5-$HT_4$ receptor agonist used for chronic constipation) (FIG. 3).

We claim:

1. A compound of formula (I)

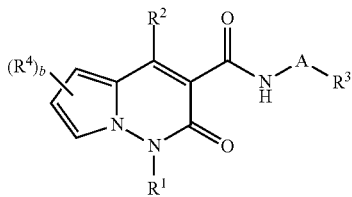

or an isotopic form, a stereoisomer or a pharmaceutically acceptable salt thereof, wherein:

$R^1$ represents hydrogen, alkyl or cycloalkyl;

$R^2$ represents hydrogen, hydroxy, halogen, alkyl or cycloalkyl;

A is heterocyclic ring selected from the group consisting of:

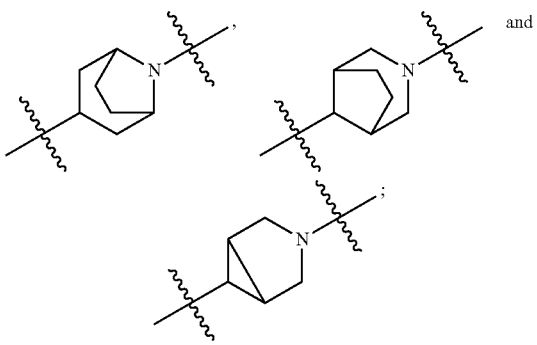

$R^3$ is hydrogen or selected from the group consisting of:

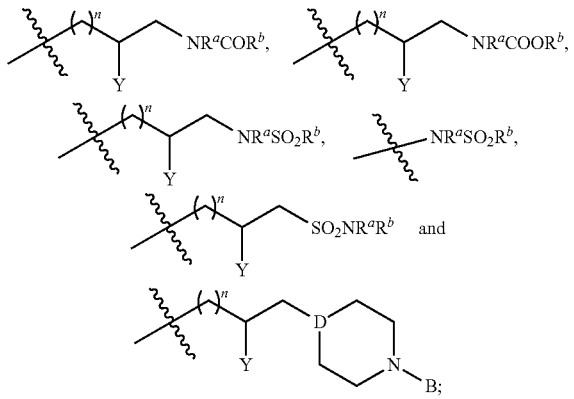

B is selected from hydrogen, alkyl, cycloalkyl, haloalkyl, hydroxyalkyl, —SO$_2$-alkyl, —COCH$_3$, —COO-alkyl, or —CO—(CH$_2$)$_m$—OH; wherein, m is an integer from 0 to 5;

Y at each occurrence is independently selected from hydrogen, hydroxy, halogen, haloalkyl, hydroxyalkyl, —COOH, —COO-alkyl, —O-alkyl, —S-alkyl or —NR$^a$R$^b$;

D represents CH or N;

n is an integer from 0 to 5;

$R^a$ at each occurrence is independently selected from hydrogen, alkyl, cycloalkyl or alkoxy;

$R^b$ at each occurrence is independently selected from hydrogen, alkyl, cycloalkyl or alkoxy;

$R^4$ represents hydrogen, hydroxy, halogen, alkyl or cycloalkyl; and b represents 1 to 3.

2. The compound of formula (I) or an isotopic form, a stereoisomer or a pharmaceutically acceptable salt thereof as claimed in claim 1, wherein, A is

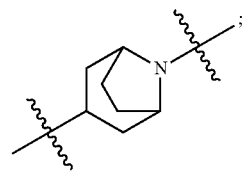 [SMILES: *C1CC2CCC(C1)N2*]

$R^2$ is hydrogen or hydroxy;

$R^3$ is selected from the group consisting of:

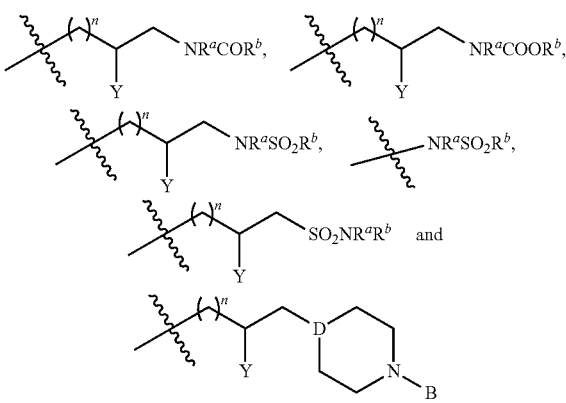

B is selected from —SO$_2$-alkyl, —COCH$_3$, —COO-alkyl, alkyl, cycloalkyl, haloalkyl, hydroxyalkyl or —CO—(CH$_2$)$_m$—OH; wherein m is an integer from 0 to 5;

Y at each occurrence is independently selected from hydrogen or hydroxy;

D represents CH or N;

n is an integer from 0 to 5;

$R^a$ at each occurrence is independently selected from hydrogen or alkyl;

$R^b$ at each occurrence is independently selected from hydrogen, alkyl, cycloalkyl or alkoxy; and $R^4$ represents hydrogen.

3. The compound of formula (I) or an isotopic form, a stereoisomer or a pharmaceutically acceptable salt thereof as claimed in claim 1, wherein the compound is selected from the group consisting of:

(R)—N-{8-[2-Hydroxy-3-[(N-methyl) methanesulfonamido]propyl]-8-azabicyclo[3.2.1]oct-3-yl}[1-isopropyl-2-oxo-1,2-dihydro pyrrolo[1,2]-bipyridazine]-3-carboxamide;

(R)—N-{8-[2-Hydroxy-3-[(N-methyl) methanesulfonamido] propyl]-8-azabicyclo[3.2.1] oct-3-yl} [1-isopropyl-2-oxo-1,2-dihydro pyrrolo[1,2-b]pyridazine]-3-carboxamide L-(+)-tartrate;

(S)—N-{8-[2-Hydroxy-3-[(N-methyl) methanesulfonamido] propyl]-8-azabicyclo[3.2.1] oct-3-yl} [1-isopropyl-2-oxo-1,2-dihydro pyrrolo[1,2-b]pyridazine]-3-carboxamide;

(S)—N-{8-[2-Hydroxy-3-[(N-methyl) methanesulfonamido] propyl]-8-azabicyclo[3.2.1] oct-3-yl} [1-isopropyl-2-oxo-1,2-dihydro pyrrolo[1,2-b]pyridazine]-3-carboxamide L-(+)-tartarate;

Racemic-N-{8-[2-Hydroxy-3-[(N-methyl) methanesulfonamido] propyl]-8-azabicyclo[3.2.1] oct-3-yl} [1-isopropyl-2-oxo-1,2-dihydro pyrrolo[1,2-b]pyridazine]-3-carboxamide;

Racemic-N-{8-[2-Hydroxy-3-[(N-methyl) methanesulfonamido] propyl]-8-azabicyclo[3.2.1] oct-3-yl} [1-isopropyl-2-oxo-1,2-dihydro pyrrolo[1,2-b]pyridazine]-3-carboxamide L-(+)-tartarate;

(R)—N-{8-[2-Hydroxy-3-[(N-methyl) methanesulfonamido] propyl]-8-azabicyclo[3.2.1] oct-3-yl} [4-hydroxy-1-isopropyl-2-oxo-1,2-dihydro pyrrolo[1,2-b]pyridazine]-3-carboxamide;

(R)—N-{8-[2-Hydroxy-3-[(N-methyl) methanesulfonamido] propyl]-8-azabicyclo[3.2.1] oct-3-yl} [4-hydroxy-1-isopropyl-2-oxo-1,2-dihydro pyrrolo[1,2-b]pyridazine]-3-carboxamide L-(+)-tartarate;

(S)—N-{8-[2-Hydroxy-3-[(N-methyl) methanesulfonamido] propyl]-8-azabicyclo[3.2.1] oct-3-yl} [4-hydroxy-1-isopropyl-2-oxo-1,2-dihydro pyrrolo[1,2-b]pyridazine]-3-carboxamide;

(S)—N-{8-[2-Hydroxy-3-[(N-methyl) methanesulfonamido] propyl]-8-azabicyclo[3.2.1] oct-3-yl} [4-hydroxy-1-isopropyl-2-oxo-1,2-dihydro pyrrolo[1,2-b]pyridazine]-3-carboxamide L-(+)-tartarate;

Racemic-N-{8-[2-Hydroxy-3-[(N-methyl) methanesulfonamido] propyl]-8-azabicyclo[3.2.1] oct-3-yl} [4-hydroxy-1-isopropyl-2-oxo-1,2-dihydro pyrrolo[1,2-b]pyridazine]-3-carboxamide;

Racemic-N-{8-[2-Hydroxy-3-[(N-methyl) methanesulfonamido] propyl]-8-azabicyclo[3.2.1] oct-3-yl} [4-hydroxy-1-isopropyl-2-oxo-1,2-dihydro pyrrolo[1,2-b]pyridazine]-3-carboxamide L-(+)-tartarate;

(R)—N-{8-[2-Hydroxy-3-(methanesulfonamido) propyl]-8-azabicyclo[3.2.1] oct-3-yl} [1-isopropyl-2-oxo-1,2-dihydro pyrrolo[1,2-b]pyridazine]-3-carboxamide;

(R)—N-{8-[2-Hydroxy-3-(methanesulfonamido) propyl]-8-azabicyclo[3.2.1] oct-3-yl} [1-isopropyl-2-oxo-1,2-dihydro pyrrolo[1,2-b]pyridazine]-3-carboxamide L-(+)-tartarate;

(R)—N-{8-[2-Hydroxy-3-[(N-methyl) acetamido] propyl]-8-azabicyclo[3.2.1] oct-3-yl} [1-isopropyl-2-oxo-1,2-dihydro pyrrolo[1,2-b]pyridazine]-3-carboxamide;

(R)—N-{8-[2-Hydroxy-3-[(N-methyl) acetamido] propyl]-8-azabicyclo[3.2.1] oct-3-yl} [1-isopropyl-2-oxo-1,2-dihydro pyrrolo[1,2-b]pyridazine]-3-carboxamide L-(+)-tartrate;

(R)—N-{8-[2-Hydroxy-3-[(1-methanesulfonyl piperazin)-4-yl] propyl]-8-azabicyclo[3.2.1] oct-3-yl} [1-isopropyl-2-oxo-1,2-dihydro pyrrolo[1,2-b]pyridazin]-3-carboxamide;

(R)—N-{8-[2-Hydroxy-3-[(1-methanesulfonyl piperazin)-4-yl] propyl]-8-azabicyclo[3.2.1] oct-3-yl} [1-isopropyl-2-oxo-1,2-dihydro pyrrolo[1,2-b]pyridazin]-3-carboxamide L-(+)tartarate;

(R)—N-{8-[2-Hydroxy-3-[(1-methanesulfonyl piperazin)-4-yl] propyl]-8-azabicyclo[3.2.1] oct-3-yl} [4-hydroxy-1-isopropyl-2-oxo-1,2-dihydro pyrrolo[1,2-b]pyridazine]-3-carboxamide;

(R)—N-{8-[2-Hydroxy-3-[(1-methanesulfonyl piperazin)-4-yl] propyl]-8-azabicyclo[3.2.1] oct-3-yl} [4-hydroxy-1-isopropyl-2-oxo-1,2-dihydro pyrrolo[1,2-b]pyridazine]-3-carboxamide L-(+)-tartarate;

N-{8-[3-[(N-Methyl) methanesulfonamido] propyl]-8-azabicyclo[3.2.1] oct-3-yl} [1-isopropyl-2-oxo-1,2-dihydro pyrrolo[1,2-b]pyridazine]-3-carboxamide;

N-{8-[3-[(N-Methyl) methanesulfonamido] propyl]-8-azabicyclo[3.2.1] oct-3-yl} [1-isopropyl-2-oxo-1,2-dihydro pyrrolo[1,2-b]pyridazine]-3-carboxamide L-(+)-tartarate;

N-{8-[3-[methanesulfonamido] propyl]-8-azabicyclo[3.2.1] oct-3-yl} [1-isopropyl-2-oxo-1,2-dihydro pyrrolo[1,2-b]pyridazine]-3-carboxamide;

N-{8-[3-[methanesulfonamido] propyl]-8-azabicyclo[3.2.1] oct-3-yl} [1-isopropyl-2-oxo-1,2-dihydro pyrrolo[1,2-b]pyridazine]-3-carboxamide L-(+)-tartarate;

N-{8-[3-Isopropylsulfonylaminopropyl]-8-azabicyclo[3.2.1] oct-3-yl} [1-isopropyl-2-oxo-1,2-dihydro pyrrolo[1,2-b]pyridazin]-3-carboxamide;

N-{8-[3-Isopropylsulfonylaminopropyl]-8-azabicyclo[3.2.1] oct-3-yl} [1-isopropyl-2-oxo-1,2-dihydro pyrrolo[1,2-b]pyridazine]-3-carboxamide L-(+)-tartarate;

N-{8-[2-Methanesulfonylaminoethyl]-8-azabicyclo[3.2.1] oct-3-yl} [1-isopropyl-2-oxo-1,2-dihydro pyrrolo[1,2-b]pyridazin]-3-carboxamide;

N-{8-[2-Methanesulfonylaminoethyl]-8-azabicyclo[3.2.1]oct-3-yl][1-isopropyl-2-oxo-1,2-dihydro pyrrolo[2-b]pyridazin]-3-carboxamide L-(+)-tartarate;

N-{8-[2-Isopropylsulfonylaminoethyl]-8-azabicyclo[3.2.1]oct-3-yl}[1-isopropyl-2-oxo-1,2-dihydro pyrrolo[2-b]pyridazin]-3-carboxamide;

N-{8-[2-Isopropylsulfonylaminoethyl]-8-azabicyclo[3.2.1]oct-3-yl}[1-isopropyl-2-oxo-1,2-dihydro pyrrolo[2-b]pyridazin]-3-carboxamide L-(+)-tartarate;

N-{8-[3-Acetamidopropyl]-8-azabicyclo[3.2.1]oct-3-yl} [1-isopropyl-2-oxo-1,2-dihydro pyrrolo[1,2-b]pyridazin]-3-carboxamide;

N-{8-[3-Acetamidopropyl]-8-azabicyclo[3.2.11 oct-3-yl}11-isopropyl-2-oxo-1,2-dihydro pyrrolo[1,2-b]pyridazin]-3-carboxamide L-(+)-tartarate;

N-{8-[3-Carbomethoxyaminopropyl]-8-azabicyclo[3.2.1]oct-3-yl}[1-isopropyl-2-oxo-1,2-dihydro pyrrolo[1,2-b]pyridazin]-3-carboxamide;

N-{8-[3-Carbomethoxyaminopropyl]-8-azabicyclo[3.2.1]oct-3-yl}[1-isopropyl-2-oxo-1,2-dihydro pyrrolo[1,2-b]pyridazin]-3-carboxamide L-(+)-tartarate;

N-{8-[2-Carbomethoxyaminoethyl]-8-azabicyclo[3.2.1] oct-3-yl}[1-isopropyl-2-oxo-1,2-dihydro pyrrolo[1,2-b]pyridazin]-3-carboxamide;

N-{8-[2-Carbomethoxyaminoethyl]-8-azabicyclo[3.2.1] oct-3-yl}[1-isopropyl-2-oxo-1,2-dihydro pyrrolo[1,2-b]pyridazin]-3-carboxamide L-(+)-tartarate;

N-{8-[2-(4-Acetyl piperazin-1-yl) ethyl]-8-azabicyclo[3.2.1]oct-3-yl}[1-isopropyl-2-oxo-1,2-dihydro pyrrolo[1,2-b]pyridazine]-3-carboxamide;

N-{8-[2-(4-Acetyl piperazin-t-yl) ethyl]-8-azabicyclo[3.2.1]oct-3-yl}[1-isopropyl-2-oxo-1,2-dihydro pyrrolo[1,2-b]pyridazine]-3-carboxamide L-(−)-tartarate;

N-{8-[2-(4-Acetyl piperazin-1-yl) ethyl]-8-azabicyclo[3.2.1]oct-3-yl}[4-hydroxy-1-isopropyl-2-oxo-1,2-dihydropyrrolo[1,2-b]pyridazine]-3-carboxamide; and N-{8-[2-(4-Acetyl piperazin-1-yl) ethyl]-8-azabicyclo[3.2.1]oct-3-yl}[4-hydroxy-1-isopropyl-2-oxo-1,2-dihydropyrrolo[1,2-b]pyridazine]-3-carboxamide L-(+)-tartrate.

4. A pharmaceutical composition comprising a therapeutically effective amount of the compound of formula (I) or a stereoisomer or a pharmaceutically acceptable salt thereof as claimed in claim 1 and pharmaceutically acceptable excipients or carriers.

5. The pharmaceutical composition as claimed in claim 4, wherein said composition is formulated to treat a gastrointestinal disease or disorder selected from irritable bowel syndrome, chronic constipation, functional dyspepsia, gastroparesis, gastroesophageal reflux disorder, post-operative ileus, intestinal pseudo-obstruction, drug-induced delayed transit, Barrett esophagus, intestinal pseudoileus, acute gastritis, chronic gastritis, gastric ulcer, duodenal ulcer, non-ulcer dyspepsia, Crohn's disease, celiac disease or delayed gastric emptying caused by gastric neurosis.

6. A method for the treatment of gastrointestinal disease or disorder related to 5-Hydroxy tryptamine 4 receptor comprising the step of administering to a patient in need thereof a therapeutically effective amount of the compound of formula (I), or a stereoisomer or a pharmaceutically acceptable salt thereof as claimed in claim 1, wherein the gastrointestinal disease or disorder is selected from irritable bowel syndrome, chronic constipation, functional dyspepsia, gastroparesis, gastroesophageal reflux disorder, post-operative ileus, intestinal pseudo-obstruction, drug-induced delayed transit, Barrett esophagus, intestinal pseudoileus, acute gastritis, chronic gastritis, gastric ulcer, duodenal ulcer, non-ulcer dyspepsia, Crohn's disease, celiac disease or delayed gastric emptying caused by gastric neurosis.

7. The method as claimed in claim 6, wherein the irritable bowel syndrome is selected from irritable bowel syndrome with predominant constipation, irritable bowel syndrome with predominant diarrhea, irritable bowel syndrome with mixed bowel habits, or unclassified irritable bowel syndrome.

* * * * *

UNITED STATES PATENT AND TRADEMARK OFFICE
CERTIFICATE OF CORRECTION

PATENT NO. : 12,275,746 B2
APPLICATION NO. : 18/724932
DATED : April 15, 2025
INVENTOR(S) : Ramakrishna Nirogi et al.

It is certified that error appears in the above-identified patent and that said Letters Patent is hereby corrected as shown below:

In the Specification

In Column 17, Line 40, please delete "H-NMR" and add --1H-NMR--.

In Column 22, Line 4, please delete "H-NMR" and add --1H-NMR--.

In Column 26, Example 3, Line 6, please delete "6.63-6.64" and add --6.63-6.65--;
Example 3, Line 7, please delete "6.85-6.85" and add --6.84-6.85--;
Example 4, Line 5, please delete ",4.40" and add --4.40--.

In Column 30, Example 11, Line 5, please delete "7.09" and add --7.99--.

In Column 35, Line 59, please delete "CD3O D" and add --CD3OD--.

In Column 36, Line 33, please delete "CD3O D" and add --CD3OD--.

In Column 37, Line 6, please delete "61" and add --6H--;
Line 7, please delete "(n, 21)" and add --(m, 2H)--;
Line 8, please delete "(n, 21)" and add --(m, 2H)--;
Line 8, please delete "(s, 31)" and add --(s, 3H)--.

In Column 38, Line 2, please delete "4H), 8.03 (s, dH)" and add --1H), 8.03 (s, 1H)--.

In Column 39, Example 27, Line 5, delete "pyridaazin" and add --pyridazin--.

In Column 40, Example 30, Line 1, please delete "CDCl3OD," and add --CD3OD--.

In Column 45, Line 26, please delete "CD3O D" and add --CD3OD--.

Signed and Sealed this
Fifteenth Day of July, 2025

Coke Morgan Stewart
*Acting Director of the United States Patent and Trademark Office*

CERTIFICATE OF CORRECTION (continued)
U.S. Pat. No. 12,275,746 B2

In Column 46, Line 25, please delete "CD3O D" and add --CD3OD--;
Line 61, please delete "10 PM" and add --10um--.

In the Claims

In Claim 3, Column 52, Line 62, please delete "pyrrolo[1,2]" and add --pyrrolo[1,2-b]--.

In Claim 3, Column 54, Line 30, please delete "[2-b]" and add --[1,2-b]--;
Line 33, please delete "[2-b]" and add --[1,2-b]--;
Line 36, please delete "[2-b]" and add --[1,2-b]--;
Line 40, please delete "[3.2.11" and add --[3.2.1]--;
Line 41, please delete "11-isopropyl" and add --[1-isopropyl--;
Line 58, please delete "piperazin-t-yl" and add --piperazin-1-yl--;
Line 60, please delete "L-(-)-tartrate" and add --L-(+)-tartrate--.